(12) United States Patent
Jansens et al.

(10) Patent No.: US 7,790,960 B2
(45) Date of Patent: Sep. 7, 2010

(54) WOUND-INDUCIBLE EXPRESSION IN PLANTS

(75) Inventors: Stefan Jansens, Ghent (BE); Miriam Hauben, Wondelgem (BE); Arlette Reynaerts, Drongen (BE)

(73) Assignee: Bayer BioScience N.V., Ghent (BE)

( * ) Notice: Subject to any disclaimer, the term of this patent is extended or adjusted under 35 U.S.C. 154(b) by 0 days.

(21) Appl. No.: 10/428,843

(22) Filed: May 5, 2003

(65) Prior Publication Data

US 2003/0221216 A1    Nov. 27, 2003

Related U.S. Application Data

(60) Provisional application No. 60/608,922, filed on May 3, 2002.

(51) Int. Cl.
*A01H 5/00*     (2006.01)
*C12N 15/82*    (2006.01)
*C12N 15/09*    (2006.01)

(52) U.S. Cl. .................. 800/302; 800/278; 800/279; 800/320.1; 800/288; 435/468

(58) Field of Classification Search .............. 800/320.1, 800/298, 302, 279, 295, 278; 435/419, 468, 435/69.1
See application file for complete search history.

(56) References Cited

U.S. PATENT DOCUMENTS

| 5,428,146 | A |   | 6/1995  | Logemann et al.   |         |
|-----------|---|---|---------|-------------------|---------|
| 5,530,197 | A | * | 6/1996  | Peferoen et al.   | 800/279 |
| 5,625,136 | A | * | 4/1997  | Koziel et al.     | 800/302 |
| 5,641,664 | A |   | 6/1997  | D'Halluin et al.  |         |
| 5,684,239 | A | * | 11/1997 | Wu et al.         | 800/301 |
| 5,689,052 | A | * | 11/1997 | Brown et al.      | 800/302 |
| 5,712,135 | A | * | 1/1998  | D'Halluin et al.  | 800/292 |
| 5,723,760 | A | * | 3/1998  | Strittmatter et al. | 800/301 |
| 5,952,547 | A |   | 9/1999  | Cornelissen et al. |        |
| 6,291,745 | B1 |  | 9/2001  | Meyer et al.      |         |
| 6,313,378 | B1 |  | 11/2001 | Baum et al.       |         |
| 6,320,100 | B1 |  | 11/2001 | Koziel et al.     |         |
| 2002/0166143 | A1 | * | 11/2002 | Bao et al.     | 800/279 |

FOREIGN PATENT DOCUMENTS

| EP | 0400246 A1 | 12/1990 |
| WO | WO 00/26378 | 5/2000 |

OTHER PUBLICATIONS

Stefan Jansens et al., "Transgenic Corn Expressing a Cry9C Insecticidal Protein from *Bacillus thuringiensis* Protected from European Corn Borer Damage", Crop Science, vol. 37, pp. 1616-1642, 1997, Crop Science America, Madison WI, USA.

Marnix Peferoen et al., "Plant Engineering for Crop Protection: Implications for Resistance Management", Chemistry of Plant Protection, 1997, vol. 13, pp. 125-156, Springer-Verlag Berlin Heidelberg.

"Advances in Insect Control: The Role of Transgenic Plants", edited by Nadine Carozzi and Michael Koziel, 1997, Taylor & Francis Ltd. Bristol, PA 19007.

Arlette Reynaerts et al., "Engineered Insect Resistance in Tomato", Acta Horticulturae vol. 376, pp. 347-352, 1994, Processing Tomato V, The International Society for Horticultural Science, The Hague, Belgium.

John Witkowski et al., "Managing Corn Borer Resistance", 1997, pp. 14-15.

J.L. Chen et al., "A Combined Use of Microprojectile Bombardment and DNA Imbibition Enhances Transformation Frequency of Canola (*Brassica napus* L.)", Theor Appl Genet (1994), vol. 88, pp. 187-192, Springer-Verlag, Vienna, Austria, New York.

Ruud A. de Maagd et al., "*Bacillus thruingiensis* Toxin-Medicated Insect Resistance in Plants" Trends in Plant Science, Jan. 1999, vol. 4, No. 1, pp. 9-13, Elsevier Science, Amsterdam, Holland.

Vaughan A. Hilder et al, "A Novel Mechanism of Insect Resistance Engineered Into Tobacco", Nature, vol. 300, Nov. 12, 1987, pp. 160-163, Nature Publishing Group, London, England.

Juan J. Estruch, "Transgenic Plants: An Emerging Approach to Pest Control", Nature Biotechnology, vol. 15, Feb. 15, 1997, pp. 137-141, Nature America, New York.

Paul C. Fox et al., "Multiple *ocs*-like Elements Required for Efficient Transcription of the Manopine Synthase Gene of T-DNA in Maize Protoplasts", Plant Molecular Biology, vol. 20, pp. 219-233, 1992, Kluwer Academic Publishers, Belgium.

Sheng Luan et al, "A Rice *cab* Gene Promoter Contains Separate cis-Acting Elements That Regular Expression in Dicot and Monocot Plants", The Plant Cell, vol. 4, pp. 971-981, Aug. 1192, American Society of Plant Physiologists, Lancaster, PA, USA.

Min Ni et al, "Strength and Tissue Specificity of Chimeric Promoters Derived from the Octopine and Mannopine Synthase Genes", The Plant Journal (1995), vol. 7, No. 4, pp. 661-676, Blackwell Sciences, Oxford, England.

Ko Shimamoto, "Gene Expression in Transgenic Monocots", Current Opinion in Biotechnology (1994) vol. 5, pp. 158-162, Current Biology Ltd, London, England.

Herman Hofte et al, "Structural and Functional Analysis of a Cloned Delta Endotoxin of *Bacillus thuringiensis* Berliner 1715", Eur. J. Biochem. (1980) vol. 161, pp. 273-280, FEBS 1986, Blackwell Science, Oxford, England.

W.H.R. Langridge et al, "Dual Promoter of *Agrobacterium tumefaciens* Mannopine Synthase Genes is Regulated by Plant Growth Hormones", Proc. Natl. Acad. Sci. USA, vol. 86, pp. 3219-3223, May 1989, Developmental Biology, National Academy of Sciences, Washington, D.C., USA.

(Continued)

*Primary Examiner*—Medina A Ibrahim
(74) *Attorney, Agent, or Firm*—Buchanan Ingersoll & Rooney PC

(57) ABSTRACT

The invention relates to a method for producing plants in which expression of an insecticidal protein is regulated by a wound-induced promoter inducing local expression to the chimeric genes used in this method and the plants obtained thereby, and to the processes for obtaining resistance to insects feeding on plants by localized expression of an insecticidal protein induced on wounding of plants by insect feeding.

27 Claims, No Drawings

OTHER PUBLICATIONS

J. Velten et al, "Isolation of a Dual Plant Promoter Fragment from the Ti Plasmid of *Agrobacterium tumefaciens*"The EMBO Journal, (1984) vol. 3, No. 12, pp. 2723-2730 , Oxford University Press, Oxford, England.

Mark Vaeck et al, "Transgenic Plants Protected from Insect Attack", Nature, vol. 328, Jul. 2, 1987, Nature Publishing Group, London, England.

Barton et al., "*Bacillus thuringiensis* δ-Endotoxin Expressed in Transgenic *Nicotiana tabacum* Provides Resistance to Lepidopteran Insects" (1987) *Plant Physiol* 85(4):1103-1109, AVI Pub. Co., Westport, Conn. USA.

Breitler et al, "The -689/+ 197 Region of the Maize Protease Inhibitor Gene Directs High Level, Wound-Inducible Expression of the *crylB* Gene Which Protects Transgenic Rice Plants From Stemborer Attack" (2001) *Mol Breeding* 7:259-274, Kluwer Academic Publishers, printed in the Netherlands.

Chen et al., "A Combined Use of Microprojectile Bombardment and DNA Imbition Enhances Transformation Frequency of Canola (*Brassica napus L.*)" (1994) *Theor Appl Genet* 88:187-192, Springer-Verlag, Berlin, Germany.

Cornelissen & Vandewiele, "Nuclear Transcriptional Activity of the Tobacco Plastid *psb*A Promoter" (1989) *Nucleic Acids Research* 17:19-23, IRL Press Limited, Oxford, England.

Datta et al., "Transformation of Rice via PEG-Mediated DNA Uptake into Protoplasts" (1999) *Methods Mol Biol* 111:335-347, Humana Press Inc., Totowa, NJ, USA.

De Greve et al., "Nucleotide Sequence and Transcript Map of the *Agrobacterium tumefaciens* Ti Plasmid-Encoded Octopine Synthase Gene" (1983) *J Mol Applied Gen* 499-511,Raven Press, New York.

De maagd et al., "*Bacillus thuringiensis* Toxin-Mediated Insect Resistance in Plants" (1999) *Trends Plant Sci* 4:9-13, Elsevier Science, Oxford, United Kingdom.

de Pater et al., "The Promoter of the Rice Gene *GOS2* is Active in Various Different Monocot Tissues and Binds Rice Nuclear Factor ASF-1" (1992) *Plant J* 2:837-844, Blackwell Sciences, Ltd., Oxford, United Kingdom.

Depicker et al., "Nopaline Synthase: Transcript Mapping and DNA Sequence" (1982) *J Mol Appl Gen* 1:561-573, Raven Press, New York.

D'Halluin et al, "Transgenic Maize Plants by Tissue Electroporation" (1992) *Plant Cell* 4:1495-1505, American Society of Plant Physiologists, Rockville, Maryland, USA.

Duan et al., "Transgenic Rice Plants Harboring an Introduced Potato Proteinase Inhibitor II Gene are Insect Resistant" (1996) *Nature Biotech* 14:494-498, Nature Publishing Group, Hampshire, United Kingdom.

Estruch et al, "Vip3A, a Novel *Bacillus thuringiensis* Vegetative Insecticidal Protein With a Wide Spectrum of Activities Against Lepidopteran Insects" (1996) *Proc Natl Acad Sci* 93:5389-5394 National Academy of Sciences, Washington, D.C., USA.

Estruch et al.,"Transgenic Plants: An Emerging Approach to Pest Control" (1997) *Nature Biotechn* 15:137-140, Nature Publishing Group, Hampshire, United Kingdom.

Forst et al., "Xenorhabdus and Photorhabdus SPP.: Bugs That Kill Bugs" (1997) *Ann Rev Microbiol* 5:47-72, Annual Reviews Inc., Palo Alto, California, USA.

Fox et al., "Multiple *ocs*-Like Elements Required for Efficient Transcription of the Mannopine Synthase Gene of T-DNA in Maize Protoplasts" (1992) *Plant Mol Biol* 20:219-233, Kluwer Academic Publishers, Printed in Belgium.

Franck et al, "Nucleotide Sequence of Cauliflower Mosaic Virus DNA" (1980) *Cell* 21:285-294, Cell Press, Cambridge, MA, USA.

Gielen et al., "The Complete Nucleotide Sequence of the TL-DNA of the *Agrobacterium tumefaciens* Plasmid pTiAch5" (1984) *EMBO J* 3:835-846, IRL Press Limited, Oxford, England.

Green and Ryan "Wound-Induced Proteinase Inhibitor in Plant Leaves: A Possible Defense Mechanism Against Insects" (1972) *Science* 175:776-777, American Association for the Advance of Science, Stamford, California, USA.

Guevara-Garcia et al., "Tissue-Specific and Wound-Inducible Pattern of Expression of the Mannopine Synthase Promoter is Determined by the Interaction Between Positive and Negative *cis*-Regulatory Elements" (1993) *Plant J* 4(3):495-505, Blackwell. Sciences Ltd., Oxford, United Kingdom.

Guthrie "Breeding for Insect Resistance in Maize" (1989) *Plant Breed Rev* 6:209-243, Timber Press, Portland, Oregon, USA.

Hilder et al., "A Novel Mechanism of Insect Resistance Engineered Into Tobacco" (1987) *Nature* 300(121:160-163, Plant Breeding institute, Trumpington, Cambridge CB2 2LQ, UK.

Höfte et al., Structural and Functional Analysis of a Cloned Delta Endotoxin of *Bacillus thuringiensis berliner* 1715 (1986) *Eur J. Biochem* 161:273-280, FEBS, West Germany.

Irie et al., "Transgenic Rice Established to Express Corn Cystatin Exhibits Strong Inhibitory Activity Against Insect Gut Proteinases" (1996) *Plant Mol Biol* 30:149-157, Kluwer Academic Publishers, Printed in Belgium.

Jansens et al., "Transgenic Corn Expressing a Cry9C Insecticidal Protein from *Bacillus thuringiensis* Protected from European Corn Borer Damage" (1997) *Crop Science* 37(5):1616-1624, Crop Science Society of America, Madison, Wisconsin, USA.

Jin et al, "Development of Transgenic Cabbage (*Brassica Oleracea* Var. *Capitata*) for Insect Resistance by *Agrobacterium Tumefaciens*-Mediated Transformation" (2000) in Vitro *Cell Devel Biol—Plant* 36:(4)231-237, Society for In Vitro Biology, Tissue Culture Associate, Columbia, MD, USA.

Langridge et al "Dual Promoter of *Agrobacterium tumefaciens* Mannopine Synthase Genes is Regulated by Plant Growth Hormones" (1989) *Proc Natl Acad Sci USA* 86:3219-3223, National Academy of Sciences, Washington, DC, USA.

Luan et al., "A Rice *cab* Gene Promoter Contains Separate *cis*-Acting Elements That Regulate Expression in Dicot and Monocot Plants" (1992) *Plant Cell* 4:971-981, American Society of Plant Physiologists, Rockville, Maryland, USA.

Ni et al., (1995) "Strength and Tissue Specificity of Chimeric Promoters Derived From the Octopine and Mannopine Synthase Genes" *Plant J* 7(4)661-676 , Blackwell Sciences, Ltd., Oxford, United Kingdom.

Odell et al. "Identification of DNA Sequences Required for Activity of the Cauliflower Mosaic Virus 35S Promoter" (1985) *Nature* 313:810-812, Nature Publishing Group, Hampshire, United Kingdom.

Peferoen, "Insect Control with Transgenic Plants Expressing *Bacillus thuringiensis* Crystal Proteins" (1997) *Advances in Insect Control: The Role of Transgenic Plants* 21-48, Taylor & Francis, London England.

Peferoen & Van Rie, "Plant Engineering for Crop Protection: Implications for Resistance Management" (1997) *Chemistry of Plant Prot* 13:125-156, Springer-Verlag, Berlin Heidelberg.

Poulsen, "Genetic Transformation of *Brassica*" (1996) *Plant Breeding* 115:209-225, Blackwell, Wissenschafts-Verlag, Berlin.

Reynaerts & Jansens, "Engineered Insect Resistance in Tomato" (1994) *Acta Horticulturae* 376:347-352, The International Society for Horticultural Science, Leuven, Belgium.

Shimamoto "Gene Expression in Transgenic Monocots" (1994) *Curr Opin Biotech* 5(2):158-162, Current Biology Ltd, London, United Kingdom.

Thompson et al., "Characterization of the Herbicide-Resistance gene *bar* from *Streptomyces hygroscopicus*" (1987) *EMBO J* 6(9):2519-2523, Oxford University Press, Oxford, United Kingdom.

Vaeck et al., "Transgenic Plants Protected from Insect Attack" (1987) *Nature* 327(6125):33-37, Nature Publishing Group, Hampshire, United Kingdom.

Velten et al. "Isolation of a Dual Plant Promoter Fragment from the Ti Plasmid of *Agrobacterium tumefaciens*" (1984) *EMBO J* 12:2733-2730, Published for the European Molecular Biology Organization, Oxford, United Kingdom.

Wilbur and Lipmann "Rapid Similarity Searches of Nucleic Acid and Protein Data Banks" (1983) Proc Natl Acad Sci USA 80:726-730, National Academy of Sciences, Washington, DC, USA.

Witowsky & Siegfried "Managing Corn Borer Resistance" (1997) *PBI Bulletin* 14-15.

Zhao et al., "Two Wound-Inducible Soybean Cysteine Proteinase Inhibitors Have Greater Insect Digestive Proteinase Inhibitory Activities than a Constitutive Homolog" (1996) *Plant Physiol* 111(4):1299-1306, American Society of Plant Physiologists, Rockville MD, USA.

Bradford, 1976, "A Rapid and Sensitive Method for the Quantitation of Microgram Quantities of Protein Utilizing the Principle of Protein-Dye Binding" Anal. Biochem. 72:248-254, Academic Press, London and New York.

Breitler et al. "The -689/+197 Region of the Maize Protease Inhibitor Gene Directs High Level, Wound-Inducible Expression of the *cry1B* Gene Which Protects Transgenic Rice Plants From Stemborer Attack", 2001, Mol Breeding 7:259-274, Kluwer Academic Publishers, Netherlands.

Clark et al., "ELISA Techniques", 1986, Methods Enzymol. 118:742-766, Academic Press, London and New York.

Crickmore et al. "Revision of the Nomenclature for the *Bacillus thuringiensis* Pesticidal Crystal Proteins" (1998) Microbiol. Mol. Biol Rev. 62(3), 807-13, American Society for Microbiology, Washington, D.C.

De Block et al, "Transformation of *Brassica napus* and *Brassica oleracea* Using *Agrobacterium tumefaciens* and the Expression of the *bar* and *neo* Genes in the Transgenic Plants", 1989, Plant Physiol 914:694-701, American Society of Plant Physiologists, Lancaster, PA.

Harpster et al., "Relative Strengths of the 35S Califlower Mosaic Virus, 1', 2', and Nopaline Synthase Promoters in Transformed Tobacco Sugarbeet and Oilseed Rape Callus Tissue", 1998, Molecular and General Genetics 121, 182-190, Springer-Verlag, Berlin and New York.

Hofte and Whiteley, "Insecticidal Crystal Proteins of *Bacillus thuringiensis*", 1989, Microbiol Rev 53(2):242- 55, American Society for Microbiology, Washington, D.C.

Mark Vaeck et al., "Transgenic Plants Protected from Insect Attack", Nature, vol. 328, Jul. 2, 1987, pp. 33-37, MacMillan Journals Ltd, London, GB.

Stefan Jansens et al, "*Phthorimaea operculella* (Lepidoptera: Gelechiidae) Resistance in Potato by Expression of the *Bacillus thuringiensis* CrylA(b) Insecticidal Crystal Protein", Journal of Economic Entomology, vol. 88, No. 5, 1995, pp. 1469-1476.

Jean Christophe Breitler et al., "The -689/+197 Region of the Maize Protease Inhibitor Gene Directs High Level, Wound-Inducible Expression of the cryl B Gene Which Protects Transgenic Rice Plants from Stemborer Attack", Molecular Breeding, vol. 7, No. 4, 2001, pp. 259-274, Kluwer Academic Publishers, The Netherlands.

T.H. Teed et al., "Gene Fusions to *lacZ* Reveal New Expression Patterns of Chimeric Genes in Transgenic Plants", The EMBO Journal, vol. 8, No. 2, pp. 343-350, 1989, Oxford University Press, Surrey, GB.

Min Ni et al., "Sequence-Specific Interactions of Wound-Inducible Nuclear Factors With Mannopine Synthase 2' Promoter Wound-Responsive Elements", Plant Molecular Biology, vol. 30, pp. 77-96, 1996, Kluwer Academic Publishers, Belgium.

Xiaolan Duan et al, "Transgenic Rice Plants Harboring an Introduced Potato Proteinase Inhibitor II Gene are Insect Resistant", Nature Biotechnology, vol. 14, Apr. 1996, pp. 494-498, Nature Publishing Co., NY USA.

Jouanin Lise et al, "Transgenic Plants for Insect Resistance", Plant Science, vol. 131, No. 1, Jan. 15, 1998, pp. 1-11, Elsevier, Limerick, Ireland.

Arturo Guevara-Garcia et al, "A 42 bp Fragment of the *pmas*1' Promoter Containing an *ocs*-Like Element Confers a Developmental, Wound- and Chemically Inducible Expression Pattern", Plant Molecular Biology vol. 38, pp. 743-753, 1998, Kluwer Academic Publishers, The Netherlands.

Kenneth A. Barton et al, "*Bacillus thuringiensis* δ-Endotoxin Expressed in Transgenic *Nicotiana tabacum* Provides Resistance to lepidopteran Insects", Plant Physiol., vol. 85, pp. 1103-1109, 1987.

Xu, Deping et al., System induction of a potato *pin2* promoter by wounding, methyl jasmonate, and abscisic acid in transgenic rice plants, Plant Molecular Biology 22: 573-588, 1993.

Meijer, E.G.M, et al., Transgenic rice cell lines and plants: expression of transferred chimeric genes, Plant Molecular Biology 16: 807-820, 1991.

Guevara-Garcia, Arturo, et al., Tissue-specific and wound-inducible pattern of expression of the mannopine synthase promoter is determined by the interaction between positive and negative *cis*-regulatory elements, The Plant Journal (1993) 4(3), 495-505.

Dekeyser, Rudy, et al., Evaluation of Selectable Markers for Rice Transformation, Plant Physiol. (1989) 90, 217-223.

Hensgens, Lambert A.M., et al., Transient and stable expression of *gusA* fusions with rice genes in rice, barley and perennial ryegrass, Plant Molecular Biology 23: 643-669, 1993.

Hensgens, Lambert A.M., et al., Transient and stable expression of *gusA* fusions with rice genes in rice, barley and perennial ryegrass, Plant Molecular Biolofy 22:1101-1127, 1993.

Van Der Leede-Plegt et al., "Introduction and Differential Use of Various Promoters in Pollen Grains of *Nicotiana Glutinosa* and *Lilium Longiflorum*", Plant Cell Reports, vol. 11, pp. 20-24 (1992).

Wilmink et al., "Expression of the GUS-Gene in the Monocot Tulip After Introduction by Particle Bombardment and *Agrobacterium*", Plant Cell Reports, vol. 11, pp. 76-80 (1992).

Meijer et al., "Transgenic Rice Cell Lines and Plants: Expression of Transferred Chimeric Genes", Plant Molecular Biology, vol. 16, pp. 807-820 (1991).

* cited by examiner

SEQUENCE LISTING

```
<160> NUMBER OF SEQ ID NOS: 3

<210> SEQ ID NO 1
<211> LENGTH: 483
<212> TYPE: DNA
<213> ORGANISM: Agrobacterium tumefaciens

<400> SEQUENCE: 1
tttcacgtgt ggaagatatg aattttttg agaaactaga taagattaat gaatatcggt        60
gttttggttt tttcttgtgg ccgtctttgt ttatattgag attttcaaa tcagtgcgca       120 agacgtgacg taagtatccg agtcagtttt tattttcta ctaatttggt cgtttatttc       180
ggcgtgtagg acatggcaac cgggcctgaa tttcgcgggt attctgtttc tattccaact      240 tttcttgat ccgcagccat taacgacttt tgaatagata cgctgacacg ccaagcctcg       300
ctagtcaaaa gtgtaccaaa caacgcttta cagcaagaac ggaatgcgcg tgacgctcgc      360
ggtgacgcca tttcgccttt tcagaaatgg ataaatagcc ttgcttccta ttatatcttc      420
ccaaattacc aatacattac actagcatct gaatttcata accaatctcg atacaccaaa     480
tcg                                                                    483

<210> SEQ ID NO 2
<211> LENGTH: 13199
<212> TYPE: DNA
<213> ORGANISM: Artificial Sequence
<220> FEATURE:
<223> OTHER INFORMATION: Sequence of plasmid pTSVH0212
<220> FEATURE:
<221> NAME/KEY: misc_feature
<222> LOCATION: (1)..(25)
<223> OTHER INFORMATION: Left border sequence of TL-DNA of pTiB6S3
<220> FEATURE:
<221> NAME/KEY: polyA_signal
<222> LOCATION: (56)..(316)
<223> OTHER INFORMATION: Fragment containing polyadenylation signals
      from the 3' untranslated region of the nopaline synthase gene
      from the T-DNA of pTiT37
<220> FEATURE:
<221> NAME/KEY: misc_feature
<222> LOCATION: (336)..(887)
<223> OTHER INFORMATION: coding sequence of phosphinothricin
      acetyltransferase of Streptomyces hygroscopicus
<220> FEATURE:
<221> NAME/KEY: promoter
<222> LOCATION: (888)..(1720)
<223> OTHER INFORMATION: Promoter region from the Cauliflower Mosaic
      virus 35S transcript (P35S)
<220> FEATURE:
<221> NAME/KEY: promoter
<222> LOCATION: (1170)..(2252)
<223> OTHER INFORMATION: TR2' promoter fragment derived from the right
      T-DNA of octopine type Agrobacterium strain ACH5
<220> FEATURE:
```

```
<221> NAME/KEY: misc_feature
<222> LOCATION: (2261)..(4114)
<223> OTHER INFORMATION: sequence encoding part of the Cry1Ab5 protein
      (Modified cry1Ab)
<220> FEATURE:
<221> NAME/KEY: polyA_signal
<222> LOCATION: (4128)..(4422)
<223> OTHER INFORMATION: Fragment containing polyadenylation signals
      from the 3'untranslated region of the octopine synthase gene from
      the TL-DNA of pTiAch5
<220> FEATURE:
<221> NAME/KEY: misc_feature
<222> LOCATION: (4470)..(4446)
<223> OTHER INFORMATION: Right border sequence of TL-DNA of pTiB6S3

<400> SEQUENCE: 2
cggcaggata tattcaattg taaatggctc catggcgatc gctctagagg atctgcgatc      60
tagtaacata gatgacaccg cgcgcgataa tttatcctag tttgcgcgct atattttgtt     120
ttctatcgcg tattaaatgt ataattgcgg gactctaatc ataaaaaccc atctcataaa     180
taacgtcatg cattacatgt taattattac atgcttaacg taattcaaca gaaattatat     240
gataatcatc gcaagaccgg caacaggatt caatcttaag aaactttatt gccaaatgtt     300
tgaacgatct gcttcggatc ctagaacgcg tgatctcaga tctcggtgac gggcaggacc     360
ggacggggcg gtaccggcag gctgaagtcc agctgccaga acccacgtc atgccagttc      420 ccgtgcttga agccggccgc cgcagcatg ccgcgggggg catatccgag cgcctcgtgc      480
atgcgcacgc tcgggtcgtt gggcagcccg atgacagcga ccacgctctt gaagccctgt     540
gcctccaggg acttcagcag gtgggtgtag agcgtggagc ccagtcccgt ccgctggtgg     600
cggggggaga cgtacacggt cgactcggcc gtccagtcgt aggcgttgcg tgccttccag     660
gggcccgcgt aggcgatgcc ggcgacctcg ccgtccacct cggcgacgag ccagggatag     720
cgctcccgca gacggacgag gtcgtccgtc cactcctgcg gttcctgcgg ctcggtacgg     780
aagttgaccg tgcttgtctc gatgtagtgg ttgacgatgg tgcagaccgc cggcatgtcc     840
gcctcggtgg cacggcggat gtcggccggg cgtcgttctg ggtccatggt tatagagaga     900
gagatagatt tatagagaga gactggtgat tcagcgtgtc cctctccaaa tgaaatgaac     960
ttccttatat agaggaaggg tcttgcgaag gatagtggga ttgtgcgtca tcccttacgt    1020
cagtggagat gtcacatcaa tccacttgct ttgaagacgg ggttggaacg tcttcttttt    1080
ccacgatgct cctcgtgggt gggggtccat ctttgggacc actgtcggca gaggcatctt    1140
gaatgatagc ctttcctttta tcgcaatgat ggcatttgta ggagccacct ccttttcta    1200 ctgtcctttc gatgaagtga cagatagctg ggcaatggaa tccgaggagg tttcccgaaa    1260
ttatcctttg ttgaaaagtc tcaatagccc tttggtcttc tgagactgta tctttgacat    1320
ttttggagta gaccagagtg tcgtgctcca ccatgttgac gaagattttc ttcttgtcat    1380
tgagtcgtaa aagactctgt atgaactgtt cgccagtctt cacggcgagt tctgttagat    1440
cctcgatttg aatcttagac tccatgcatg gccttagatt cagtaggaac tacctttta    1500 gagactccaa tctctattac ttgccttggt ttatgaagca agccttgaat cgtccatact    1560
ggaatagtac ttctgatctt gagaaatatg tctttctctg tgttcttgat gcaattagtc    1620
ctgaatcttt tgactgcatc tttaaccttc ttgggaaggt atttgatctc ctggagattg    1680
ttactcgggt agatcgtctt gatgagacct gctgcgtagg aacgcggccg ctgtacaggg    1740
cccgggcata tggcgcgcca tggttttggt ttcacgtgtg gaagatatga atttttttga    1800
gaaactagat aagattaatg aatatcggtg ttttggtttt tccttgtggc cgtctttgtt    1860
```

-continued

```
tatattgaga tttttcaaat cagtgcgcaa gacgtgacgt aagtatccga gtcagttttt    1920
attttcctac taatttggtc gtttatttcg gcgtgtagga catggcaacc gggcctgaat    1980
ttcgcgggta ttctgtttct attccaactt tttcttgatc cgcagccatt aacgactttt    2040
gaatagatac gctgacacgc caagcctcgc tagtcaaaag tgtaccaaac aacgctttac    2100
agcaagaacg gaatgcgcgt gacgctcgcg gtgacgccat ttcgcctttt cagaaatgga    2160
taaatagcct tgcttcctat tatatcttcc caaattacca atacattaca ctagcatctg    2220
aatttcataa ccaatctcga tacaccaaat cgccaaaacc atggctgaca acaaccccaa    2280
catcaacgag tgcatcccct acaactgcct gagcaaccca gaggtggagg tgctgggtgg    2340
tgagaggatc gagaccggtt acacccccat cgacatcagc ctgagcctga cccagttcct    2400
gctgagcgag ttcgtgcctg gtgctggctt cgtgctggga ctagtggaca tcatctgggg    2460
catcttcggt cccagccagt gggatgcctt cctggtgcag atcgaacagt taattaacca    2520
aagaatagaa gaattcgcta ggaaccaagc catctctaga ctggagggcc tgagcaacct    2580
gtaccagatc tacgccgaga gcttccgcga gtgggaggct gaccccacca acccagccct    2640
gcgcgaggag atgcgcatcc agttcaacga catgaactct gccctgacca ccgccatccc    2700
actcttcgct gtccagaact accaggtccc tctcctgtct gtctatgtgc aagctgccaa    2760
cctccatctc agcgtccttc gcgacgtgag cgtctttggg cagaggtggg ggttcgacgc    2820
tgccaccatc aacagccgct acaacgacct gacgcgtctg atcggcaact acaccgacca    2880
cgcagtgaga tggtacaaca ctgggcttga gagggtctgg ggtcccgaca gccgcgactg    2940
gatcaggtac aaccagttca ggcgtgaact cactctcacc gtcttggata tcgtcagtct    3000
cttccccaac tacgacagca ggacctaccc tatccggact gtgagccagc tgacccgcga    3060
gatctacacc aaccccgtgc tggagaactt cgacggcagc ttcaggggct ctgcccaggg    3120
catcgaggga agcatccgca gcccccacct gatggacatc ctgaacagca tcaccatcta    3180
cactgacgcc cacaggggtg agtactactg gtctggccac cagatcatgg cttctcccgt    3240
gggcttcagc ggtcccgagt tcaccttccc cctgtacggc acaatgggca acgctgcccc    3300
acagcagagg atcgtggccc agctgggcca gggcgtgtac cgcaccctga gcagcaccct    3360
gtacaggagg cccttcaaca tcggcatcaa caaccagcag ctgagcgtgc tggatggcac    3420
cgagttcgcc tacggcacca gcagcaacct gcccagcgcc gtataccgca agagcggcac    3480
tgtggacagc ctggacgaga tcccaccccca gaacaacaac gtgcccccta ggcagggggtt    3540
ctctcatcgc ctctcacacg tgagcatgtt ccgcagcggc ttcagcaaca gcagcgtgag    3600
catcatcagg gctcccatgt tcagctggat ccaccgcagc gctgagttca caacatcat    3660
tccaagtagc cagatcactc agatcccact caccaagagc accaacctgg gctccgggac    3720
tagcgttgtc aagggaccag ggttcactgg aggcgacatc ctgaggagga ccagcccagg    3780
ccagatcagc accttaaggg tgaacatcac cgctcccctc agccaacgct acagggtcag    3840
gatcaggtac gcttccacca ccaacctgca gttccacacc agcatcgacg gcaggcccat    3900
caaccagggc aacttcagcg ccaccatgag cagcggcagc aacctgcaga gcggaagctt    3960
ccgcactgtg ggcttcacta ccccccattcaa cttctccaac ggcagcagcg tgttcaccct    4020
gtctgcccac gtgttcaaca gcggcaacga ggtgtacatc gacaggatcg agtttgtccc    4080
agctgaggtg accttcgaag ctgagtacga ctgaggctag ctagagtcct gctttaatga    4140
gatatgcgag acgcctatga tcgcatgata tttgctttca attctgttgt gcacgttgta    4200
aaaaacctga gcatgtgtag ctcagatcct taccgccggt ttcggttcat tctaatgaat    4260
```

```
atatcacccg ttactatcgt atttttatga ataatattct ccgttcaatt tactgattgt   4320
accctactac ttatatgtac aatattaaaa tgaaaacaat atattgtgct gaataggttt   4380
atagcgacat ctatgataga gcgccacaat aacaaacaat tgcctgcagg tcgacggccg   4440
agtactggca ggatatatac cgttgtaatt tgtcgcgtgt gaataagtcg ctgtgtatgt   4500
ttgtttgatt gtttctgttg gagtgcagcc catttcaccg acaagtcgg ctagattgat    4560 ttagccctga tgaactgccg aggggaagcc atcttgagcg cggaatggga atggatttcg   4620
ttgtacaacg agacgacaga acacccacgg gaccgagctt cgaatctggc aattccggtt   4680
cgcttgctgt ccataaaacc gcccagtcta gctatcgcca tgtaagccca ctgcaagcta   4740
cctgctttct ctttgcgctt gcgttttccg gatcttcttg agatcctttt tttctgcgcg   4800
taatctgctg cttgcaaaca aaaaaaccac cgctaccagc ggtggtttgt ttgccggatc   4860
aagagctacc aactcttttt ccgaaggtaa ctggcttcag cagagcgcag ataccaaata   4920
ctgtccttct agtgtagccg tagttaggcc accacttcaa gaactctgta gcaccgccta   4980
catacctcgc tctgctaatc ctgttaccag tggctgctgc cagtggcgat aagtcgtgtc   5040
ttaccgggtt ggactcaaga cgatagttac cggataaggc gcagcggtcg ggctgaacgg   5100
ggggttcgtg cacacagccc agcttggagc gaacgaccta caccgaactg agatacctac   5160
agcgtgagct atgagaaagc gccacgcttc ccgaagggag aaaggcggac aggtatccgg   5220
taagcggcag ggtcggaaca ggagagcgca cgagggagct tccaggggga aacgcctggt   5280
atctttatag tcctgtcggg tttcgccacc tctgacttga gcgtcgattt ttgtgatgct   5340
cgtcaggggg gcggagccta tggaaaaacg ccagcaacgc ggccttttta cggttcctgg   5400
ccttttgctg gccttttgct cacatgttct ttcctgcgtt atccctgat tctgtggata    5460 accgtattac cgcctttgag tgagctgata ccgctcgccg cagccgaacg accgagcgca   5520
gcgagtcagt gagcgaggaa gcggaagagc gcctgatgcg gtattttctc cttacgcatc   5580
tgtgcggtat ttcacaccgc atatggtgca ctctcagtac aatctgctct gatgccgcat   5640
agttaagcca gtatacactc cgctatcgct acgtgactgg gtcatggctg cgccccgaca   5700
cccgccaaca cccgctgacg cgccctgacg ggcttgtctg ctcccggcat ccgcttacag   5760
acaagctgtg accgtctccg ggagctgcat gtgtcagagg ttttcaccgt catcaccgaa   5820
acgcgcgagg cagggtgcct tgatgtgggc gccggcggtc gagtggcgac ggcgcggctt   5880
gtccgcgccc tggtagattg cctggccgta ggccagccat ttttgagcgg ccagcggccg   5940
cgataggccg acgcgaagcg gcggggcgta gggagcgcag cgaccgaagg gtaggcgctt   6000
tttgcagctc ttcggctgtg cgctggccag acagttatgc acaggccagg cgggttttaa   6060
gagttttaat aagttttaaa gagttttagg cggaaaaatc gccttttttc tcttttatat   6120
cagtcactta catgtgtgac cggttcccaa tgtacggctt tgggttccca atgtacgggt   6180
tccggttccc aatgtacggc tttgggttcc caatgtacgt gctatccaca ggaaagagac   6240
cttttcgacc ttttttccct gctagggcaa tttgccctag catctgctcc gtacattagg   6300
aaccggcgga tgcttcgccc tcgatcaggt tgcggtagcg catgactagg atcgggccag   6360
cctgccccgc ctcctccttc aaatcgtact ccggcaggtc atttgacccg atcagcttgc   6420
gcacggtgaa acagaacttc ttgaactctc cggcgctgcc actgcgttcg tagatcgtct   6480
tgaacaacca tctggcttct gccttgcctg cggcgcggcg tgccaggcgg tagagaaaac   6540
ggccgatgcc gggatcgatc aaaaagtaat cggggtgaac cgtcagcacg tccgggttct   6600
```

```
tgccttctgt gatctcgcgg tacatccaat cagctagctc gatctcgatg tactccggcc    6660
gcccggtttc gctctttacg atcttgtagc ggctaatcaa ggcttcaccc tcggataccg    6720
tcaccaggcg gccgttcttg gccttcttcg tacgctgcat ggcaacgtgc gtggtgttta    6780
accgaatgca ggtttctacc aggtcgtctt tctgctttcc gccatcggct cgccggcaga    6840
acttgagtac gtccgcaacg tgtggacgga acacgcggcc gggcttgtct cccttccctt    6900
cccggtatcg gttcatggat tcggttagat gggaaaccgc catcagtacc aggtcgtaat    6960
cccacacact ggccatgccg gccggccctg cggaaacctc tacgtgcccg tctggaagct    7020
cgtagcggat caccctcgcca gctcgtcggt cacgcttcga cagacggaaa acggccacgt    7080
ccatgatgct gcgactatcg cgggtgccca cgtcatagag catcggaacg aaaaaatctg    7140
gttgctcgtc gcccttgggc ggcttcctaa tcgacgcgc accggctgcc ggcggttgcc    7200
gggattcttt gcggattcga tcagcggccg cttgccacga ttcaccgggg cgtgcttctg    7260
cctcgatgcg ttgccgctgg gcggcctgcg cggccttcaa cttctccacc aggtcatcac    7320
ccagcgccgc gccgatttgt accgggccgg atggtttgcg accgtcacgc cgattcctcg    7380
ggcttggggg ttccagtgcc attgcagggc cggcagacaa cccagccgct tacgcctggc    7440
caaccgcccg ttcctccaca catggggcat tccacggcgt cggtgcctgg ttgttcttga    7500
ttttccatgc cgcctccttt agccgctaaa attcatctac tcatttattc atttgctcat    7560
ttactctggt agctgcgcga tgtattcaga tagcagctcg gtaatggtct tgccttggcg    7620
taccgcgtac atcttcagct tggtgtgatc ctccgccggc aactgaaagt tgaccccgctt   7680 catggctggc gtgtctgcca ggctggccaa cgttgcagcc ttgctgctgc gtgcgctcgg    7740
acggccggca cttagcgtgt ttgtgctttt gctcattttc tctttacctc attaactcaa    7800
atgagttttg atttaatttc agcggccagc gcctggacct cgcgggcagc gtcgccctcg    7860
ggttctgatt caagaacggt tgtgccggcg cggcagtgc ctgggtagct cacgcgctgc    7920
gtgatacggg actcaagaat gggcagctcg tacccggcca gcgcctcggc aacctcaccg    7980
ccgatgcgcg tgcctttgat cgcccgcgac acgacaaagg ccgcttgtag ccttccatcc    8040
gtgacctcaa tgcgctgctt aaccagctcc accaggtcgg cggtggccca tatgtcgtaa    8100
gggcttggct gcaccggaat cagcacgaag tcggctgcct tgatcgcgga cacagccaag    8160
tccgccgcct ggggcgctcc gtcgatcact acgaagtcgc gccggccgat ggccttcacg    8220
tcgcggtcaa tcgtcgggcg gtcgatgccg acaacggtta gcggttgatc ttcccgcacg    8280
gccgcccaat cgcgggcact gccctgggga tcggaatcga ctaacagaac atcggccccg    8340
gcgagttgca gggcgcgggc tagatggggt gcgatggtcg tcttgcctga cccgcctttc    8400
tggttaagta cagcgataac cttcatgcgt tccccttgcg tatttgttta tttactcatc    8460
gcatcatata cgcagcgacc gcatgacgca agctgtttta ctcaaataca catcacccttt   8520 ttagacggcg cgctcggtt tcttcagcgg ccaagctggc cggccaggcc gccagcttgg     8580
catcagacaa accggccagg atttcatgca gccgcacggt tgagacgtgc gcgggcggct    8640
cgaacacgta cccggccgcg atcatctccg cctcgatctc ttcggtaatg aaaaacggtt    8700
cgtcctggcc gtcctggtgc ggtttcatgc ttgttcctct tggcgttcat tctcggcggc    8760
cgccagggcg tcggcctcgg tcaatgcgtc ctcacggaag gcaccgcgcc gcctggcctc    8820
ggtgggcgtc acttcctcgc tgcgctcaag tgcgcggtac agggtcgagc gatgcacgcc    8880
aagcagtgca gccgctcttt tcacggtgcg gccttcctgg tcgatcagct cgcgggcgtg    8940
cgcgatctgt gccggggtga gggtagggcg ggggccaaac ttcacgcctc gggccttggc    9000
```

```
ggcctcgcgc ccgctccggg tgcggtcgat gattagggaa cgctcgaact cggcaatgcc   9060
ggcgaacacg gtcaacacca tgcggccggc cggcgtggtg gtgtcggccc acggctctgc   9120
caggctacga aggcccgcgc cggcctcctg gatgcgctcg gcaatgtcca gtaggtcgcg   9180
ggtgctgcgg gccaggcggt ctagcctggt cactgtcaca acgtcgccag ggcgtaggtg   9240
gtcaagcatc ctggccagct ccgggcggtc gcgcctggtg ccgtgatct tctcggaaaa    9300
cagcttggtg cagccggccg cgtgcagttc ggcccgttgg ttggtcaagt cctggtcgtc   9360
ggtgctgacg cgggcatagc ccagcaggcc agcggcggcg ctcttgttca tggcgtaatg   9420
tctccggttc tagtcgcaag tattctactt tatgcgacta aaacacgcga caagaaaacg   9480
ccaggaaaag ggcagggcgg cagcctgtcg cgtaacttag gacttgtgcg acatgtcgtt   9540
ttcagaagac ggctgcactg aacgtcagaa gccgactgca ctatagcagc ggaggggttg   9600
gatcgatccc tgctcgcgca ggctgggtgc caagctctcg ggtaacatca aggcccgatc   9660
cttggagccc ttgccctccc gcacgatgat cgtgccgtga tcgaaatcca gatccttgac   9720
ccgcagttgc aaaccctcac tgatccgtcg acgcgtttaa tgaccagcac agtcgtgatg   9780
gcaaggtcag aatagcgctg aggtctgcct cgtgaagaag gtgttgctga ctcataccag   9840
gcctgaatcg ccccatcatc cagccagaaa gtgagggagc cacggttgat gagagctttg   9900
ttgtaggtgg accagttggt gattttgaac ttttgctttg ccacggaacg gtctgcgttg   9960
tcgggaagat gcgtgatctg atccttcaac tcagcaaaag ttcgatttat tcaacaaagc  10020
cacgttgtgt ctcaaaatct ctgatgttac attgcacaag ataaaatat atcatcatga   10080
acaataaaac tgtctgctta cataaacagt aatacaaggg gtgttatgag ccatattcaa  10140
cgggaaacgt cttgctcgag gccgcgatta aattccaaca tggatgctga tttatatggg  10200
tataaatggg ctcgcgataa tgtcgggcaa tcaggtgcga caatctatcg attgtatggg  10260
aagcccgatg cgccagagtt gtttctgaaa catggcaaag gtagcgttgc caatgatgtt  10320
acagatgaga tggtcagact aaactggctg acggaattta tgcctcttcc gaccatcaag  10380
cattttatcc gtactcctga tgatgcatgg ttactcacca ctgcgatccc cgggaaaaca  10440
gcattccagg tattagaaga atatcctgat tcaggtgaaa atattgttga tgcgctggca  10500
gtgttcctgc gccggttgca ttcgattcct gtttgtaatt gtccttttaa cagccgcgta  10560
tttcgtctcg ctcaggcgca atcacgaatg aataacggtt tggttgatgc gagtgatttt  10620
gatgacgagc gtaatggctg gcctgttgaa caagtctgga agaaatgca taaacttttg   10680
ccattctcac cggattcagt cgtcactcat ggtgatttct cacttgataa ccttattttt   10740
gacgagggga aattaatagg ttgtattgat gttggacgag tcggaatcgc agaccgatac  10800
caggatcttg ccatcctatg gaactgcctc ggtgagtttt ctccttcatt acagaaacgg  10860
ctttttcaaa aatatggtat tgataatcct gatatgaata aattgcagtt tcatttgatg  10920
ctcgatgagt ttttctaatc agaattggtt aattggttgt aacactggca gagcattacg  10980
ctgacttgac gggacggcgg ctttgttgaa taaatcgaac ttttgctgag ttgaaggatc  11040
agatcacgca tcttcccgac aacgcagacc gttccgtggc aaagcaaaag ttcaaaatca  11100
ccaactggtc cacctacaac aaagctctca tcaaccgtgg ctccctcact ttctggctgg  11160
atgatggggc gattcaggcc tggtatgagt cagcaacacc ttcttcacga ggcagacctc  11220
agcgctattc tgaccttgcc atcacgactg tgctggtcat taaacgcgtc gacccgttcc  11280
atacagaagc tgggcgaaca aacgatgctc gccttccaga aaaccgagga tgcgaaccac  11340
```

-continued

```
ttcatccggg gtcagcacca ccggcaagcg cccggacggc cgaggtcttc cgatctcctg    11400
aagccagggc agatccgtgc acagcacttg ccgtagaaga acagcaaggc cgccaatgcc    11460
tgacgatgcg tggagaccga aaccttgcgc tcgttcgcca gccaggacag aaatgcctcg    11520
acttcgctgc tgcccaaggt tgccgggtga cgcacaccgt ggaaacggat gaaggcacga    11580
acccagtgga cataagcctg ttcggttcgt aagctgtaat gcaagtagcg tatgcgctca    11640
cgcaactggt ccagaacctt gaccgaacgc agcggtggta acggcgcagt ggcggttttc    11700
atggcttgtt atgactgttt ttttgggta cagtctatgc ctcgggcatc caagcagcaa     11760
gcgcgttacg ccgtgggtcg atgtttgatg ttatggagca gcaacgatgt tacgcagcag    11820
ggcagtcgcc ctaaaacaaa gttaaacatc atgagggaag cggtgatcgc cgaagtatcg    11880
actcaactat cagaggtagt tggcgtcatc gagcgccatc tcgaaccgac gttgctggcc    11940
gtacatttgt acggctccgc agtggatggc ggcctgaagc cacacagtga tattgatttg    12000
ctggttacgg tgaccgtaag gcttgatgaa acaacgcggc gagctttgat caacgacctt    12060
ttggaaactt cggcttcccc tggagagagc gagattctcc gcgctgtaga agtcaccatt    12120
gttgtgcacg acgacatcat tccgtggcgt tatccagcta agcgcgaact gcaatttgga    12180
gaatggcagc gcaatgacat tcttgcaggt atcttcgagc cagccacgat cgacattgat    12240
ctggctatct tgctgacaaa agcaagagaa catagcgttg ccttggtagg tccagcggcg    12300
gaggaactct ttgatccggt tcctgaacag gatctatttg aggcgctaaa tgaaaacctta   12360 acgctatgga actcgccgcc cgactgggct ggcgatgagc gaaatgtagt gcttacgttg    12420
tcccgcattt ggtacagcgc agtaaccggc aaaatcgcgc cgaaggatgt cgctgccgac    12480
tgggcaatgg agcgcctgcc ggcccagtat cagcccgtca tacttgaagc tagacaggct    12540
tatcttggac aagaagaaga tcgcttggcc tcgcgcgcag atcagttgga agaatttgtc    12600
cactacgtga aaggcgagat caccaaggta gtcggcaaat aatgtctaac aattcgttca    12660
agccgacgcc gcttcgcggc gcggcttaac tcaagcgtta gatgcactaa gcacataatt    12720
gctcacagcc aaactatcag gtcaagtctg ctttattat ttttaagcgt gcataataag     12780
ccctacacaa attgggagat atatcatgaa aggctggctt tttcttgtta tcgcaatagt    12840
tggcgaagta atcgcaacat ccgcattaaa atctagcgag gctttactaa gctagcttg    12900 cttggtcgtt ccggtaccgt gaacgtcggc tcgattgtac ctgcgttcaa atactttgcg    12960
atcgtgttgc gcgcctgccc ggtgcgtcgg ctgatctcac ggatcgactg cttctctcgc    13020
aacgccatcc gacggatgat gtttaaaagt cccatgtgga tcactccgtt gccccgtcgc    13080
tcaccgtgtt gggggaagg tgcacatggc tcagttctca atggaaatta tctgcctaac     13140
cggctcagtt ctgcgtagaa accaacatgc aagctccacc gggtgcaaag cggcagcgg    13199
```

<210> SEQ ID NO 3
<211> LENGTH: 1854
<212> TYPE: DNA
<213> ORGANISM: Artificial sequence
<220> FEATURE:
<223> OTHER INFORMATION: sequence encoding modified cry1Ab protein

<400> SEQUENCE: 3

```
atggctgaca acaacccaa catcaacgag tgcatcccct acaactgcct gagcaaccca      60
gaggtggagg tgctgggtgg tgagaggatc gagaccggtt acacccccat cgacatcagc    120
ctgagcctga cccagttcct gctgagcgag ttcgtgcctg gtgctggctt cgtgctggga    180
ctagtggaca tcatctgggg catcttcggt cccagccagt gggatgcctt cctggtgcag    240
```

-continued

```
atcgaacagt taattaacca aagaatagaa gaattcgcta ggaaccaagc catctctaga    300
ctggagggcc tgagcaacct gtaccagatc tacgccgaga gcttccgcga gtgggaggct    360
gaccccacca acccagccct gcgcgaggag atgcgcatcc agttcaacga catgaactct    420
gccctgacca ccgccatccc actcttcgct gtccagaact accaggtccc tctcctgtct    480
gtctatgtgc aagctgccaa cctccatctc agcgtccttc gcgacgtgag cgtctttggg    540
cagaggtggg ggttcgacgc tgccaccatc aacagccgct acaacgacct gacgcgtctg    600
atcggcaact acaccgacca cgcagtgaga tggtacaaca ctgggcttga gagggtctgg    660
ggtcccgaca gccgcgactg gatcaggtac aaccagttca ggcgtgaact cactctcacc    720
gtcttggata tcgtcagtct cttccccaac tacgacagca ggacctaccc tatccggact    780
gtgagccagc tgacccgcga gatctacacc aaccccgtgc tggagaactt cgacggcagc    840
ttcaggggct ctgcccaggg catcgagggc agcatccgca gcccccacct gatggacatc    900
ctgaacagca tcaccatcta cactgacgcc cacagggtg agtactactg gtctggccac     960
cagatcatgg cttctcccgt gggcttcagc ggtcccgagt tcaccttccc cctgtacggc    1020
acaatgggca acgctgcccc acagcagagg atcgtggccc agctgggcca gggcgtgtac    1080
cgcaccctga gcagcaccct gtacaggagg cccttcaaca tcggcatcaa caaccagcag    1140
ctgagcgtgc tggatggcac cgagttcgcc tacggcacca gcagcaacct gcccagcgcc    1200
gtataccgca agagcggcac tgtggacagc ctggacgaga tcccacccca gaacaacaac    1260
gtgccccta ggcagggggtt ctctcatcgc ctctcacacg tgagcatgtt ccgcagcggc    1320
ttcagcaaca gcagcgtgag catcatcagg gctcccatgt tcagctggat ccaccgcagc    1380
gctgagttca acaacatcat tccaagtagc cagatcactc agatcccact caccaagagc    1440
accaacctgg gctccgggac tagcgttgtc aagggaccag ggttcactgg aggcgacatc    1500
ctgaggagga ccagcccagg ccagatcagc accttaaggg tgaacatcac cgctcccctc    1560
agccaacgct acagggtcag gatcaggtac gcttccacca ccaacctgca gttccacacc    1620
agcatcgacg gcaggcccat caaccagggc aacttcagcg ccaccatgag cagcggcagc    1680
aacctgcaga gcggaagctt ccgcactgtg ggcttcacta ccccattcaa cttctccaac    1740
ggcagcagcg tgttcacccct gtctgcccac gtgttcaaca gcggcaacga ggtgtacatc    1800
gacaggatcg agtttgtccc agctgaggtg accttcgaag ctgagtacga ctga          1854
```

WOUND-INDUCIBLE EXPRESSION IN PLANTS

CONTINUING APPLICATION DATA

This application is a continuation-in-part of U.S. Application Ser. No. 60/608,922, filed May 3, 2002, the contents of which are incorporated herein by reference.

FIELD OF THE INVENTION

The invention relates to a method for producing plants in which expression of an insecticidal protein is regulated by a wound-induced promoter inducing local expression to the chimeric genes used in this method and the plants obtained thereby, and to the processes for obtaining resistance to insects feeding on plants by localized expression of an insecticidal protein induced on wounding of plants by insect feeding.

BACKGROUND ART

Most successful attempts to make plants that are resistant to insect attack have been obtained by, and are believed to be dependent on, high level expression of insecticidal toxins (Estruch et al., 1997; Witowsky & Siegfried, 1997). Most particularly for the Bt toxins, which as full-length proteins were found to be expressed poorly in plants, efforts have concentrated on increasing expression of these toxins in plants by use of strong constitutive promoters and by modification of the genes encoding them (Vaeck et al., 1987; Barton et al., 1987). More recently spatial regulation of expression of the insecticidal protein in those tissues susceptible to attack or triggered by feeding of the insect has been suggested as possibly providing advantages for resistance management (Peferoen & Van Rie, 1997). One of the major conditions for obtaining regulatory approval for transgenic insect resistant plants is the availability of an insect resistance management strategy. The currently favored strategy is the combination of 100% toxicity of the transgenic plants to the target pest(s), obtained by high dose expression of a specific toxin and this during the full life-cycle of the pest, with the use of refuges of non-transgenic plants, which allow the maintenance of the target pest population (De Maagd et al. 1999). In order to be able to comply with such a strategy, the use of strong constitutive promoters in the engineering of insect-resistant plants has further been encouraged.

Inducible expression of insect resistance has primarily been examined for the potato proteinase-inhibitor genes (pin1 and pin2), which are part of the natural defense system in plants and upon wounding, ensure the generation of a systemic signal throughout the plants (Green and Ryan, 1972; Hilder et al. 1987). Introduction of the pin2 gene in rice resulted in high-level systemic accumulation of the protein in rice plants, which showed increased resistance to major pests (Duan et al., 1996). Breitler et al. (2001) describes the use of the C1 region of the maize proteinase inhibitor (MPI) gene to drive wound-inducible expression of the cry1B coding sequence in rice and the first transformants were found to effectively protect rice against stemborer attack, the wound-induced expression was described to be both locally and systemically.

In a small-scale laboratory experiment, transgenic cabbage leaves transformed with the cry1Ab3 gene placed under the control of the inducible vspB promoter from soybean were as toxic to diamondback moth as those transformed with the same gene under control of the 35S promoter, but wound-inducibility was not demonstrated (Jin et al., 2000).

The TR2' promoter of the mannopine synthase gene of *Agrobacterium tumefaciens*, originally considered to direct constitutive expression (Velten et al. 1984; Vaeck et al. 1987), has been used to direct wound-inducible expression of a native Cry1Ab gene in tomato, which led to relatively low expression and only moderate insect control (Reynaerts & Jansens, 1994). Though a possible broad application for expression of Bt proteins has been suggested (Peferoen, 1997), there appear to be discrepancies between the reports on the expression pattern of the TR2' promoter in tobacco and other dicots (Ni et al. 1995). In general, the use of monocot promoters is preferred for optimal expression of genes in monocots (Shimamoto, 1994) and certain promoters have been found to have different cis-acting elements in monocots and dicots (Luan et al. 1992). The contribution of different elements of the TR2' promoter on its activity was investigated in maize protoplasts (Fox et al., 1992), but there have been no reports on the expression pattern of the TR2' promoter in a monocotyledonous plant. Furthermore, the strongest deletion mutant was found to be 20 times less active than the CaMV 35S promoter (Fox et al., 1992).

*Agrobacterium mannopine* synthase promoters have been characterized as being constitutive, root-specific, and tissue-specific promoters, e.g., see U.S. Pat. Nos. 6,291,745, 6,320,100 and 6,313,378. In U.S. Pat. No. 5,641,664, it is believed that various constitutive and organ- and tissue-specific promoters that are used to direct expression of genes in transformed dicotyledonous plants will also be suitable for use in transformed monocots. As part of a general list of suitable foreign constitutive promoters for transforming plant cells in this patent are the TR1' and the TR2' promoters which drive the expression of the 1' and 2' genes, respectively, of the T-DNA of Agrobacterium, and are said to be wound-induced promoters. This patent shows no monocot plant transformed with the TR2' or TR1' promoter, nor is there any suggestion that these promoters are wound-induced promoters in monocot plants or are useful for expression of an insecticidal protein in a monocot plant.

The present invention describes how the TR2' promoter can be used to direct wound-induced expression of an insecticidal protein in monocot plants to obtain insect resistance. Such wound-inducible expression of the TR2' promoter leads to a strong but localized increase of expression of the insecticidal protein. The putative effect on plant vigor and growth, observed with high level expression of some Bt proteins particularly upon repeated inbreeding (such as reported in WO 00/26378 for Cry2Ab) is likely to be reduced as the limited expression of the protein should minimize any burden on functions important for maintaining the agronomic qualities of the engineered crop. This is also an important factor when stacking of different traits (or different Bt proteins) is envisaged. As high-dose expression levels are attained upon contact with the target pest, such plants should comply with current IRM strategies. Additionally, the combination of the specificity of the insect toxin produced with a spatially and temporally limited expression pattern (i.e. in tissues susceptible to wounding, upon wounding) is likely to reduce exposure of non-target organisms, which can be considered advantageous over constitutive production of the toxin by the plants. Thus, an effective system of regulated expression ensuring effective insect resistance for major crops such as corn and rice is of interest from both a regulatory and agricultural point of view.

SUMMARY OF THE INVENTION

The present invention relates to a method for obtaining wound-induced expression of an insecticidal protein in a monocot plant, which method comprises introducing into the genome of the plant a foreign DNA which is a chimeric gene comprising a DNA sequence encoding the insecticidal protein under control of a promoter region comprising the TR2' promoter. According to a particular embodiment of the invention, the insecticidal protein is a *Bacillus thuringiensis* toxin. The insecticidal protein may be active against pests of monocot plants, such as the insecticidal Cry1Ab, Cry1F, Cry2Ae, Cry9C or Cry2Ab protein or an insecticidal fragment or mutant thereof.

Thus, one embodiment of the present invention relates to a method for obtaining insect resistance, which may be high dose insect resistance, in plants, plant cells or plant tissues, including monocotyledonous plants, (e.g., gramineae), particularly corn, plants, plant cells or plant tissues, by providing the plants, plant cells or tissue with a foreign DNA comprising a DNA sequence encoding an insecticidal protein under control of a promoter region comprising the TR2' promoter. According to the present invention the TR2' promoter is used to increase expression of the insecticidal protein upon wounding, e.g. by insect feeding. Thus, according to a particular embodiment of the invention, expression of the insecticidal protein in monocotyledonous plants, which may be measured in the greenhouse by, e.g., an ELISA assay, is low (i.e., below 0.005% total soluble protein (mean value of multiple measurements taken from several, e.g., at least 3 or at least 5, plants of the same transformation event) in leaves, in the absence of wounding or infestation and is increased, e.g., doubled, or even increased 5 to 100 fold, in the wounded or infested tissues, such as leaves, within 24 hours.

In one embodiment of the present invention, a chimeric gene comprising a DNA sequence encoding an insecticidal protein under control of the wound-inducible TR2' promoter is used to confer insect resistance to monocotyledonous plants, especially to graminae, such as corn, by directing local expression of the insecticidal protein at the site of insect feeding. Thus, the invention relates to chimeric genes for obtaining wound-inducible expression in monocot plants. In one embodiment of the invention, expression (as measured in the greenhouse) is low or not detectable (less than 0.005% of total soluble protein (mean value of multiple measurements taken from several, e.g., at least 3, or at least 5, plants of the same event)) in leaves of non-wounded, non-infected plants, and, upon infection, increased levels of insecticidal protein (at least double, or at least from 5 to 100 fold increase or more) are induced locally in the infected tissues, within about 18 hours. According to this aspect of the invention, plants, such as monocotyledonous plants, are provided that are insect resistant due to the presence in their genome of a foreign DNA comprising a DNA sequence encoding an insecticidal protein, under the control of the TR2' promoter which ensures expression in wounded tissues. According to one embodiment of the invention, expression of an insecticidal protein in the plants is such that, in the absence of wounding of the plant (e.g., when grown in the greenhouse) the insecticidal protein is expressed at low or undetectable levels (e.g. below 0.005% of total soluble protein (mean value of multiple measurements taken from several (e.g., at least 3, or at least 5), plants of the same event) in leaves, stalk, seed and/or pollen and, upon feeding by insects, is increased in the wounded tissue to a level which is sufficient to kill the feeding pest, for example to a concentration of at least 0.01% of total soluble protein.

According to one embodiment of the invention the TR2' promoter is used in monocotyledonous plants to confer insect resistance by directing wound-inducible expression of an insecticidal protein which is a Bt toxin. Examples of such DNA sequences encoding Bt toxins are well known in the art and are described herein.

According to one embodiment of the present invention use of the TR2' promoter in corn to direct wound-inducible expression of a Bt toxin is particularly suited to engineer resistance of corn against the European Corn Borer (ECB), based on the local high-dose expression of the toxin in the plant upon feeding by target insects. The plants or plant parts (cells or tissues) of the present invention, comprising in their genome a foreign DNA comprising a DNA sequence encoding an insecticidal protein under the control of the TR2' promoter, upon wounding produce levels of insecticidal protein that are toxic to ECB larvae, including for example to ECB larvae of the fourth stage as can be determined by insect efficacy assays described herein. It is possible to obtain mortality rates of ECB fourth instar larvae of at least 97%, at least 99%, or even of 100%.

The present invention further relates to monocotyledonous plants that are resistant to insects, while expressing very low basal levels of insecticidal protein in non-wounded leaves of the plant. According to one aspect of this invention, monocotyledonous plants such as corn are obtained which combine efficient insect resistance with optimal agronomic characteristics, without penalty on agronomic performances due to expression of the insecticidal protein, as can be ascertained by assessing plant phenotype, segregation, emergence, vigor and/or agronomic ratings.

According to another aspect of this invention, monocotyledonous plants such as corn plants are obtained that are insect resistant and particularly suited for stacking with other traits (e.g. other types of insect resistance, herbicide resistance or agronomic traits).

According to another aspect of the invention, monocotyledonous plants, such as corn plants are provided, which are resistant to (a) target pest(s), but for which production of the insecticidal protein in, for example, leaves and/or pollen, is low to undetectable in the absence of wounding, limiting exposure of non-target organisms to the insecticidal protein.

According to the present invention, the plants with the characteristics described above are obtained by introduction into the genome of the plant of a DNA sequence encoding an insecticidal protein under control of the TR2' promoter which is demonstrated to function as wound-inducible promoter in monocotyledonous plants, more particularly in corn plants.

DETAILED DESCRIPTION

The term "gene" as used herein refers to any DNA sequence comprising several operably linked DNA fragments such as a promoter region, a 5' untranslated region (the 5'UTR), a coding region (which may or may not code for a protein), and an untranslated 3' region (3'UTR) comprising a polyadenylation site. Typically, in plant cells, the 5'UTR, the coding region and the 3'UTR are transcribed into an RNA of which, in the case of a protein encoding gene, the coding region is translated into a protein. A gene may include additional DNA fragments such as, for example, introns. While a promoter region is required in a gene used for transformation in the current invention, the 3' UTR comprising a polyadenylation site need not be present in the transferred gene itself, but can be found in the upstream plant DNA sequences after insertion of a gene not containing a 3' UTR comprising a polyadenylation site. Similarly, a coding sequence of this invention can be inserted in the plant genome downstream of an existing plant promoter so that expression of the insecticidal protein of the invention occurs from such reconstituted chimeric gene in the plant (e.g., as in promoter tagging experiments).

The term "chimeric" when referring to a gene or DNA sequence refers to a gene or DNA sequence which comprises at least two functionally relevant DNA fragments (such as promoter, 5'UTR, coding region, 3'UTR, intron) that are not naturally associated with each other and/or originate, for example, from different sources. "Foreign" referring to a gene or DNA sequence with respect to a plant species is used to indicate that the gene or DNA sequence is not naturally found in that plant species, or is not naturally found in that genetic locus in that plant species. The term "foreign DNA" will be used herein to refer to a DNA sequence as it has incorporated into the genome of a plant as a result of transformation in that plant or in a plant from which it is a progeny.

A genome of a plant, plant tissue or plant cell, as used herein, refers to any genetic material in the plant, plant tissue or plant cell, and includes both the nuclear and the plastid and mitochondrial genome.

A "fragment" or "truncation" of a DNA molecule or protein sequence as used herein refers to a portion of the original DNA or protein sequence (nucleic acid sequence or amino acid sequence) referred to or a synthetic version thereof (such as a sequence which is adapted for optimal expression in plants), which can vary in length but of which the minimum size is sufficient to ensure the (encoded) protein to be biologically active, the maximum size not being critical. A "variant" or "mutant" of a sequence is used herein to indicate a DNA molecule or protein of which the sequence (nucleic or amino acid) is essentially identical to the sequence to which the term refers.

Sequences which are "essentially identical" are similar to such a degree that when two sequences are aligned, the percent sequence identity, i.e. the number of positions with identical nucleotides or amino acids divided by the number of nucleotides or amino acids in the shorter of the sequences, is higher than 70%, higher than 85%, higher than 90%, higher than 95%, or is between 96 and 100%. The alignment of two nucleotide sequences is performed by the algorithm as described by Wilbur and Lipmann (1983) using a window size of 20 nucleotides, a word length of 4 nucleotides, and a gap penalty of 4.

'Insecticidal' is used herein to mean toxic to insects that are crop pests. In the context of the present invention, target insects may be the pests of monocotyledonous plants, such as corn. Crop pests include, but are not limited to, major lepidopteran pests, such as *Ostrinia nubilalis* (European corn borer or ECB), *Sesamia nonagrioides* (Mediterranean Stalk borer) and *Helicoverpa zea* (corn earworm), and major coleopteran pests, such as *Diabrotica* spp. insects, particularly *Diabrotica virgifera virgifera* and *Diabrotica undecimpunctata howardi* (Corn rootworm).

An 'insecticidal protein' or 'toxin' as used herein should be understood as a protein, polypeptide or peptide which is toxic to insects. Examples of such an insecticidal protein are the Bt Cry toxins, mutants or insecticidal fragments thereof (such as those reviewed by Höfte and Whiteley, 1989, in Crickmore et al. (1998) and described in WO 00/26378, WO 97/40162, and U.S. Pat. No. 6,023,013), more particularly the Cry2Ae (WO 02/057664) protein or an insecticidal fragment thereof, the Cry2Ab protein or an insecticidal fragment thereof, the Cry9C protein or fragments or mutants thereof (e.g., as described in WO94/24264 or WO99/00407), the Cry1F protein or an insecticidal fragment thereof, and the Cry1Ab protein or an insecticidal fragment thereof, as well as the 149B1 combined (about 14 and 44 kilodalton) toxins or insecticidal fragments thereof, and the Cry3Bb protein and insecticidal fragments or mutants thereof as described in U.S. Pat. Nos. 6,548,291, 6,063,597 and 6,501,009. Other insecticidal proteins are for instance the VIPs, particularly VIP3A, more particularly VIP3Aa, VIP3Ab and VIP3Ac proteins or insecticidal fragments thereof (Estruch et al., 1996, WO 96/10083, U.S. Pat. Nos. 6,429,360, 5,877,012), or the proteins encoded by the mis, war and sup sequences (WO98/18932, WO99/57282), and the toxins isolated from *Xhenorabdus* and *Photorabdus* ssp. such as those produced by *Photorabdus luminescens* (Forst et al., 1997). Other insecticidal proteins include, but are not limited to, the potato proteinase inhibitor I and II, the cowpea proteinase inhibitor, the cystein proteinase inhibitor of soybean (Zhao et al., 1996) or the cystatins such as those isolated from rice and corn (Irie et al., 1996), cholesterol oxidases, chitinases, and lectins. An insecticidal protein can be a protoxin (i.e., the primary translation product of a full-length gene encoding an insecticidal protein). Also included are equivalents and variants, derivatives, truncations or hybrids of any of the above proteins which have insecticidal activity. A Bt toxin, or Bt protein, as used herein refers to an insecticidal protein as previously defined which is directly or indirectly derived (e.g., modified so as to improve expression in plants or toxicity to insects) from a protein naturally produced by *Bacillus thuringiensis* and comprises a sequence which is essentially identical to the toxic fragment of a naturally produced Bt toxin, or at least a domain thereof. A Bt toxin or Bt protein, as used herein, can be a crystal protein or an insecticidal part thereof, or can be a non-crystal protein such as a secreted protein or a protein produced mainly during the vegetative phase of a Bt strain, or can be an insecticidal mutant or part thereof. 'A DNA encoding an insecticidal protein' as used herein includes a truncated, modified, synthetic or naturally occurring DNA sequence, encoding an insecticidal protein.

In a particular embodiment of the present invention, the DNA encoding an insecticidal protein is a DNA sequence encoding a Bt toxin, more preferably a DNA sequence modified to increase expression of the insecticidal protein in plants. According to a particular embodiment of the present invention the DNA sequence encoding an insecticidal protein is a modified cry1Ab DNA sequence which encodes at least part of the Cry1Ab5 protein described by Höfte et al. (1986), preferably a DNA sequence encoding a protein comprising the amino acid sequence from an amino acid position between amino acid positions 1-28 to an amino acid between amino acid positions 607-725 thereof, for example comprising amino acids 1-616. The encoded modified Cry1Ab protein may also have an insertion of an alanine codon (GCT) behind the ATG start codon (AlaAsp2 . . . Asp616).

The expression level of an insecticidal protein in plant material can be determined in a number of ways described in the art, such as by quantification of the mRNA encoding the insecticidal protein produced in the tissue using specific primers (such as described by Cornelissen & Vandewiele, 1989), or by direct specific detection of the amount of insecticidal protein produced, e.g., by immunological detection methods. More particularly, according to the present invention the expression level of insecticidal protein is expressed as the percentage of soluble insecticidal protein as determined by immunospecific ELISA as described herein related to the total amount of soluble protein (as determined, e.g., by Bradford analysis (Bradford, 1976)). An ELISA that is useful in the current invention may be a sandwich ELISA (Clark et al., 1986).

A 'wound-inducible' promoter or a promoter directing an expression pattern which is wound-inducible as used herein means that, at least in the leaves, upon wounding expression of the coding sequence under control of the promoter is significantly increased, i.e. is at least doubled, may be 5 times increased, or even 20 to 100 times increased. 'Wounding' as used herein is intended to mean either mechanical damage or perforation of at least the plant epidermis or outer cell layer by any kind of insect feeding, wounding as used herein can also be simulated by cutting a leaf with a sharp instrument such as a scalpel. Preferably, according to the present invention, wound-inducible expression of an insecticidal protein, such as a Bt insecticidal protein, in a plant means that basal expression (i.e., in the absence of wounding, preferably as measured in the greenhouse) of the protein in the leaves of the plant at V4 stage is low, for example below 0.005% total soluble protein content (mean value of measurements taken from several plants of one transformation event), and, upon wounding rises, for example to a level above 0.01% of total soluble protein, or alternatively to a level of 0.04% to 0.5% total soluble protein content or higher as measured using a leaf part that was detached after wounding and then incubated in vitro for several hours, e.g., about 12 to about 60 hours, or alternatively about 18 to about 20 hours. Measurements made using an excised in vitro leaf assay (in such assay an excised leaf or part thereof is incubated in vitro (e.g., in a petri dish on humid filter paper) in a greenhouse or growth chamber at room temperature for several hours, e.g., about 12 to 60 hours, alternatively about 18 to 20 hours, after wounding (to better reflect the conditions upon insect feeding) typically will give a higher induction of expression than measurements after wounding in planta without in vitro incubation of a detached leaf or a part thereof. Wound-induced protein levels are typically lower (but still significantly higher than non-induced background levels) when measured around 12 to 60 hours, or alternatively when measured around 18 to 20 hours, after wounding of a plant leaf without excising the leaf part for in vitro incubation. For any of the measurements on insecticidal protein concentration in plant tissue, such as leaves, after wounding, and for measuring the increase in expression as described herein, the detached tissue, e.g., leaf, may be used in conduction an assay with in vitro incubation, which reflects the actual concentration induced in the tissue upon insect feeding (control leaves are fresh, unwounded and undergo no in vitro incubation to better reflect the actual concentration in the plant tissues). Basal or background expression levels of a wound-induced promoter, as used herein, may be measured from freshly excised, not previously wounded, leaf material taken from greenhouse-grown plants. According to a particular embodiment of the invention, expression of the insecticidal protein at least in the wounded leaves rises to 0.1% total soluble protein content at the site of wounding. It is believed that the percentage of insecticidal protein per total soluble protein in accordance with the invention that is actually ingested by an insect upon insect feeding is higher than the percentage measured in the plant or part thereof, due to the localized expression and the fact that only induced (wounded) tissue will be ingested by the insect. Also, for measurement of protein concentration a certain minimum amount of plant tissue is excised (typically about 2-3 mm around the wound is excised for leaves), to run the insecticidal protein content analysis, hence the presence of unwounded cells is believe to decrease the percentage of insecticidal protein per total soluble protein extracted from the sample.

As typically observed in transformation experiments of this kind, a range of different plant transformation events is obtained after transformation, and a selection procedure may be employed to select the best plants for further development (i.e., for crossing into suitable plant lines adapted to a certain growing region). In such a selection procedure, plants are selected showing low or undetectable protein levels in plant tissue, e.g., in leaves and/or pollen, which plants upon wound-induction show at least a 5-fold increase in expression in leaves.

A "greenhouse", as used herein, refers to a relatively stable growing environment for plants which shields plants from normal field conditions, with no or little infestation by insects, rabbits, birds or other animals or external factors (such as wind or storms) which can damage a crop plant in the field. A typical greenhouse is largely made out of transparent materials such as glass or plastic, so as to allow natural daylight to reach the plants, and can have regulated light, growth medium (soil or an artificial medium), water and nutrient supply and/or temperature control. The term "greenhouse," as used herein, also includes rooms or boxes with no daylight, as long as a light source and a growth medium is provided so that normal plant growing conditions are established. As such, a greenhouse is the most suitable place to measure basal or background expression levels in leaves for the wound-inducible constructs of this invention (in a non-induced state), for comparative purposes.

While similar basal or background expression values of insecticidal protein can be found in leaves of plants in a field, it is expected that infestation by insects or mechanical damage, e.g., by vehicles, rabbits or birds to the plants in a field will increase the expression level by induction of the wound-inducible promoter of this invention, and hence not a real basal level will typically be measured in all plants in a field.

'High dose' expression, or 'high dose' insect resistance, as used herein when referring to a plant, preferably a monocot plant in accordance with this invention, refers to a concentration of the insecticidal protein in a plant (measured by ELISA as a percentage of the total soluble protein, which total soluble protein is measured after extraction of soluble proteins in an extraction buffer (e.g., the extraction buffer described in Jansens et al., 1997) using Bradford analysis (Bio-Rad, Richmond, Calif.; Bradford, 1976)) which kills a developmental stage of the target insect that is significantly less susceptible, e.g., between 25 to 100 times less susceptible to the toxin than the first larval stage of the insect and can thus can be expected to ensure full control of the target insect. A high dose insect resistance is the obtaining of, for example, at least 97 percent, or at least 99 percent, or 100 percent, mortality for the fourth larval instar (for insects having 5 larval instars) or the last larval instar (for insects having 4 or less larval instars) of a target insect, as measured 10 to 14 days after insect infestation of such plant in standard insect bioassays, such as whole plant bioassays, of a plant having high dose expression or high dose insect resistance. The existence of one target insect species (i.e., an insect species which can cause commercially significant damage to a plant species or variety, and which is typically an insect for which a transgenic plant is developed) for which a transformed plant according to this invention provides a high dose insect resistance is sufficient for a plant to be designated as giving "high dose" expression in accordance with this invention. Also included in this invention are also the plant cells or plant tissues, such as corn plant cells or corn plant tissues, whether contained in a plant or present in an in vitro culture, transformed with the wound-induced chimeric gene of the invention, that have a high dose insect resistance as described above using insect bio-assays.

High dose when referring to ECB control in corn as used herein refers to the production of insecticidal protein by the plant in mid-whorl stage in an amount that is toxic to ECB larvae of the L4 stage (European Corn Borer. Ecology and Management. 1996. North Central Regional Extension Publication No. 327. Iowa State University, Ames, Iowa) as can be determined by toxicity assays with artificial infestation described herein, wherein mortality of at least 90%, or at least 97%, or at least 99%, or 100% of the L4 ECB larvae is obtained in a test 14 days, or 10 days, after infestation of the plants with L4 larvae. Surprisingly, a high dose expression of an insecticidal protein is obtained in the corn plants of the invention using the TR2' promoter to drive wound-induced expression, even when expression is low or undetectable by sensitive ELISA protocols in an non-induced state, and expression is only induced upon insect feeding. As is common in plant transformation experiments, some of the plants obtained after transformation will not be suitable for further development, and suitable plant lines with low basal or background expression and high dose wound-induced expression will need to be selected from the transformation events obtained; such a plant line may contain only one inserted DNA encoding an insecticidal protein. Typically, commercially acceptable plant lines are obtained from over one hundred, preferably from several hundreds, of initial transformed plants.

According to the present invention 'wound-inducible' expression is furthermore preferably characterized in that the effect of the promoter is local, i.e., is confined essentially to those cells or tissues directly affected by wounding or immediately surrounding the wounded tissue. This as opposed to a systemic effect, which directly or indirectly (through a cascade of reactions) ensures a widespread effect, such as widespread expression of proteins involved in the natural defense mechanisms of the plant. Expression of the insecticidal protein in undamaged tissues of the plant may be, on average, not more than 0.01% of the total soluble protein concentration, or alternatively not more than 0.005% total soluble protein (mean value of multiple measurements taken from several, e.g., at least 3, or at least 5, plants from one transformation event), as measured by ELISA (see above) in greenhouse-grown plants. In one embodiment of this invention, wound-inducible promoter activity in leaves, such as corn leaves, is localized to the region of wounding, and will not be detected (using ELISA assays) in a region of the plant, such as the leaf, more than 10 cm, or alternatively more than 2 cm, distant of the wounding site (e.g., not in a leaf lower or higher than the wounded leaf in the same plant, nor in the same leaf more then 10 cm, or alternatively more than 2 cm, away from the wounded site on the leaf). This effectively limits expression in the plant, including the leaves, such as corn leaves, to those places where expression is needed (i.e., where an insect feeds or at least perforates leaf tissue in an attempt to feed) and hence minimizes stress on the plant that could be caused by high-level constitutive expression. Particularly when stacking several genes encoding different proteins (e.g., different insect control proteins) in one plant, wound-induced expression of one or more of the introduced genes is believed to be beneficial.

In another embodiment, the wound-induced expression of an insecticidal protein in accordance with this invention is characterized by a quick induction of expression, rising from basal or background level to a higher protein level (e.g., at least twice the amount in the controls, or at least 5 to 100 times the amount in the controls) at around 18 to 24 hours, e.g., at 18, 20 or 24 hours, after wounding using an assay wherein a leaf part is wounded, cut out of the leaf and incubated in vitro for that period of time. The basal or background level is measured in freshly excised and not in previously wounded leaf parts, which are not incubated in vitro.

The "TR2' promoter" as used herein relates to any promoter comprising the TR2' (or mannopine synthase, abbreviated as mas) functional part of the TR1'-TR2' dual promoter element from Agrobacterium (Velten et al. 1984; Langridge et al. 1989). Thus this can comprise the TR2' element either alone or in combination with the divergent TR1' element (Guevara-Garcia et al., 1998) or other (regulatory) elements, including but not limited to enhancer regions, introns and the like, as long as the wound-induction promoter characteristics in accordance with the present invention are substantially retained. In a preferred embodiment of this invention, transcription is directed from the TR2' promoter region (and the coding sequence is hence operably linked to and downstream of the TR2' promoter sequence), even if the TR1'-TR2' dual promoter (or any part thereof retaining the TR2' promoter element) is used. Most particularly, the TR2' promoter as used herein refers to a promoter region comprising a fragment of SEQ ID NO:1 spanning from a nucleotide position between nucleotide positions 1 and 336 to nucleotide position 483, and which may comprise the sequence of nucleotides 96 to 483 of SEQ ID NO:1, or alternatively comprising SEQ ID NO: 1 or a functional equivalent thereof, i.e., a modification thereof capable of directing wound-induced expression in plants, e.g., in monocotyledonous plants. Such functional equivalents include sequences which are essentially identical to a nucleotide sequence comprising at least nucleotides 328 to 483 (comprising the TR2' promoter element, Velten et al., 1984) of SEQ ID NO: 1. Such sequences can be isolated from different Agrobacterium strains. Alternatively such functional equivalents correspond to sequences which can be amplified using oligonucleotide primers comprising at least about 25, at least about 50, or up to 100 consecutive nucleotides of nucleotides 328 to 483 of SEQ ID NO:1 in a polymerase chain reaction. Functional equivalents of the TR2' promoter can also be obtained by substitution, addition or deletion of nucleotides of the sequence of SEQ ID NO:1 and include hybrid promoters comprising the functional TR2' part of SEQ ID NO:1. Such promoter sequences can be partly or completely synthetic.

The plants of the present invention are protected against insect pests, by the wound-inducible expression of a controlling amount of insecticidal protein. By controlling is meant a toxic (lethal) or combative (sub-lethal) amount. Upon induction, a high dose (as hereinbefore defined) may be produced. At the same time, the plants should be morphologically normal and may be cultivated in a usual manner for consumption and/or production of products. Furthermore, said plants should substantially obviate the need for chemical or biological insecticides (to insects targeted by the insecticidal protein).

Different assays can be used to measure the effect of the insecticidal protein expression in the plant. For example, the toxicity of the insecticidal protein produced in a corn plant to Ostrinia nubilalis or ECB (also referred to herein as ECB efficacy) can be assayed in vitro by testing of protein extracted from the plant in feeding bioassays with ECB larvae or by scoring mortality of larvae distributed on leaf material of transformed plants in a petri dish (both assays described by Jansens et al., 1997). In the field, first brood ECB larvae (ECB1) infestation is evaluated based on leaf damage ratings (Guthrie, 1989) while evaluation of the total number of stalk tunnels per plant and stalk tunnel length are indicative of second brood ECB (ECB2) stalk feeding damage (see, e.g., Jansens et al., 1997 for stalk tunnel length analysis).

The plants of the present invention optionally also comprise in their genome a gene encoding herbicide resistance. For example, the herbicide resistance gene may be the bar or the pat gene, which confers glufosinate tolerance to the plant, i.e. the plants are tolerant to the herbicide Liberty™. Tolerance to Liberty™ can be tested in different ways. For instance, tolerance can be tested by Liberty™ spray application. Spray treatments should be made between the plant stages V2 and V6 for best results. Tolerant plants are characterized by the fact that spraying of the plants with at least 200 grams active ingredient/hectare (g.a.i./ha), 400 g.a.i./ha, and possibly up to 1600 g.a.i./ha (4× the normal field rate), does not kill the plants. A broadcast application should be applied at a rate of 28-34 oz Liberty™+3 lbs Ammonium Sulfate per acre. It is best to apply at a volume of 20 gallons of water per acre using a flat fan type nozzle while being careful not to direct spray applications directly into the whorl of the plants to avoid surfactant burn on the leaves. The herbicide effect should appear within 48 hours and be clearly visible within 5-7 days. Examples of other herbicide resistance genes are the genes encoding resistance to phenmedipham (such as the pmph gene, U.S. Pat. No. 5,347,047; U.S. Pat. No. 5,543,306), the genes encoding resistance to glyphosate (such as the EPSPS genes, U.S. Pat. No. 5,510,471), genes encoding bromoxynil resistance (such as described in U.S. Pat. No. 4,810,648) genes encoding resistance to sulfonylurea (such as described in EPA 0 360 750), genes encoding resistance to the herbicide dalapon (such as described in WO 99/27116), and genes encoding resistance to cyanamide (such as described in WO 98/48023 and WO 98/56238) and genes encoding resistance to glutamine synthetase inhibitors, such as PPT (such as described in EP-A-0 242 236, EP-A-0 242 246, EP-A-0 257 542).

According to one embodiment of the invention, the chimeric gene comprising a DNA encoding an insecticidal protein under control of the TR2' promoter can be introduced (simultaneously or sequentially) in combination with other chimeric genes into a plant, to obtain different traits in the plant (also referred to as 'stacking'). Similarly, the plant of the invention containing a chimeric gene comprising a DNA encoding an insecticidal protein under control of the TR2' promoter, is particularly suited for combination with other traits. Such other traits include, but are not limited to traits such as those encoded by chimeric genes which confer insect resistance, herbicide resistance, stress or drought tolerance, or traits which modify other agronomic characteristics of the plant. Such a trait can also encompass the synthesis of a product to be recovered from the plant.

Introduction of a foreign DNA or a chimeric gene into the genome of a plant, cell or tissue can be achieved in different ways and is not critical to the present invention. Successful genetic transformation of monocots has been obtained by a number of methods including *Agrobacterium*-mediated transformation (as described, for example for corn in U.S. Pat. No. 6,074,877 or U.S. Pat. No. 6,140,553); microprojectile bombardment (as described, for example by Chen et al., 1994); direct DNA uptake into protoplasts (as described, for example by Data et al. 1999; Poulsen, 1996); and electroporation (D'Halluin et al., 1992).

The following non-limiting examples describe the construction of chimeric genes comprising a DNA sequence encoding an insecticidal protein under control of the TR2' promoter, for expression in plants and insect resistant plants obtained therewith. Unless stated otherwise in the Examples, all recombinant DNA techniques are carried out according to standard protocols as described in Sambrook and Russell (2001) Molecular Cloning: A Laboratory Manual, Third Edition, Cold Spring Harbor Laboratory Press, NY, in Volumes 1 and 2 of Ausubel et al. (1994) Current Protocols in Molecular Biology, Current Protocols, USA and in Volumes I and II of Brown (1998) Molecular Biology LabFax, Second Edition, Academic Press (UK). Standard materials and methods for plant molecular work are described in Plant Molecular Biology Labfax (1993) by R. D. D. Croy, jointly published by BIOS Scientific Publications Ltd (UK) and Blackwell Scientific Publications, UK. Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

Throughout the description and Examples, reference is made to the following sequences represented in the sequence listing:

| | |
|---|---|
| SEQ ID NO: 1: | nucleotide sequence of a preferred embodiment of the TR2' promoter |
| SEQ ID NO: 2: | sequence of pTSVH0212 |
| SEQ ID NO: 3: | sequence of a modified cry1Ab coding sequence |

EXAMPLES

Example 1

Generation of Events with a Foreign Gene Under Control of the TR2' Promoter

Development of Events

For the evaluation of wound-induced expression of a DNA sequence encoding an insecticidal gene, a construct was made comprising a promoter region comprising the TR2' promoter (Velten et al. 1984) directing the expression of a modified cry1Ab protein. The plasmid pTSVH0212 containing the genes of interest placed between the T-DNA borders (also referred to as 'TR2'-Cry1Ab') was used for *Agrobacterium*-mediated transformation (WO 98/37212).

| | | |
|---|---|---|
| PTSVH0212 | 3'nos-bar-p35S3><Tr2'-modcry1Ab-3'ocs | (SEQ ID NO: 2) |

The structure of the PTSVH0212 construct is provided in Table 1. For control plants with constitutive expression of the insecticidal protein, transformations were performed with constructs comprising a DNA sequence encoding the modified Cry1Ab protein under control of either the 35S promoter from Cauliflower Mosaic Virus (Franck et al. 1980)(referred to as 35S-cry1Ab), or the promoter of the GOS2 gene from rice (de Pater et al., 1992) with the cab22 leader from Petunia (Harpster et al. 1988)(also referred to as 'Gos/cab-cry1Ab') or the 5' leader sequence of the GOS2 gene from rice, containing the second exon, the first intron and the first exon of the GOS transcript (de Pater et al., 1992)(referred to as 'Gos/gos-cry1Ab'). All constructs included the 35S-bar gene.

TABLE 1

Nucleotide positions of the genetic elements in pTSVH0212 (TR2'-cry1Ab)

| Nt positions | Direction | Description and references |
|---|---|---|
| 25-1 | Counter clockwise | Left Border sequence of TL-DNA of pTiB6S3 (Gielen et al., 1984). Synthetic polylinker sequence |
| 316-56 | Counter clockwise | Fragment containing polyadenylation signals from the 3' untranslated region of the nopaline synthase gene from the T-DNA of pTiT37 (Depicker et al., 1982). Synthetic polylinker sequence |
| 887-336 | Counter clockwise | bar: the coding sequence of phosphinothricin acetyl transferase of *Streptomyces hygroscopicus* (Thompson et al., 1987) |
| 1720-888 | Counter clockwise | P35S3: promoter region from the Cauliflower Mosaic Virus 35S transcript (Odell et al., 1985). Synthetic polylinker sequence |
| 2252-1770 | Counter clockwise | TR2' Promoter fragment derived from the right T-DNA of octopine type Agrobacterium strain ACH5 (Velten et al., 1984) Synthetic polylinker sequence |
| 2261-4114 | | Modified cry1Ab: The modified cry1Ab coding sequence encodes part of the Cry1Ab5 protein described by Höfte et al. (1986) and has an insertion of an alanine codon (GCT) 3' of the ATG start codon (SEQ ID NO: 3). Synthetic polylinker sequence |
| 4128-4422 | | Fragment containing polyadenylation signals from the 3' untranslated region of the octopine synthase gene from the TL-DNA of pTiAch5 (De Greve et al., 1983). Synthetic polylinker sequence |
| 4470-4446 | Counter clockwise | Right Border sequence of TL-DNA of pTiB6S3 (Gielen et al., 1984). |

Regenerated plantlets were selected based on tolerance to Liberty™.

Evaluation of Events

The *Agrobacterium* transformants were checked for presence of vector sequence at the left border of the T-DNA. Southern blot analyses were performed with leaf material of the primary transformants (T0).

Example 2

Wound-Induced Expression of an Insecticidal Protein

Basal Expression of the Insecticidal Protein

The basal level of expression of the modified Cry1Ab insecticidal protein was determined by a Cry1Ab sandwich ELISA with a polycondensated IgG fraction of a polyclonal rabbit antiserum against Cry1Ab as first antibody and a monoclonal antibody against Cry1Ab as second antibody, after extraction of soluble protein using the extraction method and buffer described in Jansens et al., 1997. Samples of leaves at V3 stage plants, pollen and leaf of R1 stage plants and leaves, stalk and pollen at harvest were taken of plants in the greenhouse (corn stages are as determined in 'How a Corn Plant Develops, Special Report No. 48, Iowa State University of Science and Technology, Cooperative Extension Service, Ames, Iowa, Reprinted June 1993; see also the internet website containing the relevant information at:

http://www.extension.iastate.edu/pages/hancock/agriculture/corn/corn_develop/CornGro wthStages.html:). As a comparison, samples were taken from plants transformed with the Gos/gos-cry1Ab constructs.

Results are provided in Table 2 as percentage of detected Cry1Ab protein per total soluble protein (measured using the Bradford assay (Bio-Rad, Richmond, Calif.; Bradford, 1976)). The mean value represents the average of 5 samples taken from different plant lines of one transformation event.

TABLE 2

Expression of Cry1Ab protein in different tissues of plants transformed with the TR2'-cry1Ab and Gos/gos-cry1Ab constructs

| Event (construct) | | V3 stage Leaf | R1 stage Leaf | R1 stage Pollen | Harvest Leaf | Harvest Stalk | Harvest Pollen |
|---|---|---|---|---|---|---|---|
| WI602-0402 (TR2-cry1Ab) | Mean st. dev. | 0 | 0 0 | 0.000 0.000 | 0.000 0.000 | 0.010 0.010 | 0.000 0.010 |
| WI604-1602 (TR2'-cry1Ab) | Mean st. dev. | 0 0 | 0 0 | 0.000 0.000 | 0.000 0.000 | 0.010 0.010 | 0.000 0.000 |
| WI606-0802 (TR2'-cry1Ab) | Mean st. dev. | 0 0 | 0 0 | 0.000 0.000 | 0.000 0.000 | 0.020 0.040 | 0.000 0.000 |
| WI606-1206 (TR2'-cry1Ab) | Mean st. dev. | 0 0 | 0 0 | 0.000 0.000 | 0.000 0.000 | 0.010 0.010 | 0.000 0.000 |
| WI600-0218 (TR2'-cry1Ab) | Mean st. dev. | 0 0 | 0 0 | 0.000 0.000 | | | |
| WI602-0802 (TR2'-cry1Ab) | Mean st. dev. | 0 0 | 0 0 | 0.000 0.000 | 0.000 0.000 | 0.010 0.010 | 0.010 0.010 |
| CE2168-0202 (Gos/gos-cry1Ab) | Mean st. dev. | 0.31 0.04 | 0.26 0.06 | 0.040 0.010 | 0.230 0.060 | 0.800 0.360 | 0.030 0.010 |
| CE2168-1602 (Gos/gos-cry1Ab) | Mean st. dev. | 0.34 0.04 | 0.23 0.05 | 0.050 0.020 | 0.270 0.150 | 0.870 1.450 | 0.030 0.010 |

For the plants obtained from transformation with the TR2'-cry1Ab construct, mean values for the basal expression of the modified Cry1Ab protein in the greenhouse were found to be below detection limit (0.001% or 0.000% of total soluble protein) in all leaf samples taken from plants at V3 stage, R1 stage or at harvest. Average basal expression of the insecticidal protein in the stalk was found to be around 0.01% total soluble protein content for most plants at harvest. In plants obtained with the Gos/gos-cry1Ab construct, expression of the Cry1Ab protein was above 0.2% in all leaf samples and up to more than 1% in some of the stalk samples taken at harvest.

Wound-Induced Expression of the Insecticidal Protein.

Studies were performed in the greenhouse to determine the expression of the insecticidal Cry1Ab protein upon mechanical damage in non-transformed plants, plants obtained with the TR2'-cry1Ab construct and plants obtained with the Gos/cab-cry1Ab construct. Leaves and roots were damaged by cutting. Wounding was made on fully expanded leaves, each mm a perpendicular cut was made with a scalpel on the leaf without damaging the mid-rib. Leaf samples were taken before and 18 h after mechanical damage. Cry1Ab protein levels were measured by ELISA (Table 3) on excised leaf parts.

of around 0.5% in the leaves of V3 plants, irrespective of wounding. During flowering and harvest, expression levels of around 0.1-0.2% were measured before and after wounding.

A similar assay, wherein wounding was in planta (without in vitro incubation of an excised leaf part) on greenhouse-grown plants, resulted in lower expression values, with still a marked increase in expression on wounding shown.

In this assay, second instar ECB larvae were placed in clip-cages on five corn plants of WI602-0402 in VT stage. Of each plant, sixty hours later, samples were taken of the damaged leaf area in the clip-cage, from leaf 2 cm or 10 cm up and down of the clip-cage, and from a leaf above and beneath the leaf with the clip-cage. Leaf samples were also collected at the start of the experiment. Cry1Ab ELISA was run on the samples, mean (bold) and standard deviation were calculated. Results are shown in Table 4 below.

TABLE 3 expression of insecticidal protein in different plant parts before and after mechanical wounding

| | | Cry1Ab in % soluble protein/total protein | | | | | | | | |
|---|---|---|---|---|---|---|---|---|---|---|
| | | V4 stage | | Flowering | | | | | Harvest | |
| Event | | Leaf | | Leaf | | Root | | | | |
| (construct) | | Leaf | induced | Leaf | induced | root | induced | Pollen | Leaf | Stalk | Kernel |
| WI600-0218 | Mean | 0.000 | 0.020 | 0.000 | 0.020 | 0.023 | 0.036 | 0.000 | 0.000 | 0.000 | 0.000 |
| (TR2'-Cry1Ab) | st. dev. | 0.000 | 0.008 | 0.000 | 0.007 | 0.008 | 0.011 | 0.000 | 0.000 | 0.000 | 0.000 |
| WI606-0406 | Mean | 0.005 | 0.046 | 0.000 | 0.007 | 0.012 | 0.008 | 0.000 | \ | 0.002 | 0.002 |
| (TR2'-Cry1Ab) | st. dev. | 0.007 | 0.005 | 0.000 | 0.006 | 0.009 | 0.009 | 0.000 | | 0.004 | |
| WI604-1602 | Mean | 0.002 | 0.104 | 0.001 | 0.020 | 0.020 | 0.024 | 0.000 | 0.004 | 0.004 | 0.001 |
| (TR2'-Cry1Ab) | st. dev. | 0.003 | 0.012 | 0.000 | 0.009 | 0.008 | 0.008 | 0.000 | 0.002 | 0.003 | 0.000 |
| WI606-0802 | Mean | 0.003 | 0.064 | 0.001 | 0.010 | 0.027 | 0.037 | 0.000 | 0.002 | 0.004 | 0.003 |
| (TR2'-Cry1Ab) | st. dev. | | 0.004 | 0.000 | 0.009 | 0.012 | 0.020 | 0.000 | 0.001 | 0.003 | 0.001 |
| WI606-1206 | Mean | 0.001 | 0.081 | 0.000 | 0.022 | 0.032 | 0.024 | 0.000 | 0.004 | 0.002 | 0.001 |
| (TR2'-Cry1Ab) | st. dev. | | 0.016 | 0.000 | 0.010 | 0.005 | 0.011 | 0.000 | 0.003 | 0.001 | 0.001 |
| CE048-2402 | Mean | 0.83 | 0.614 | 0.280 | 0.397 | 0.196 | 0.253 | 0.000 | 0.376 | 1.120 | 0.047 |
| (35S-Cry1Ab) | st. dev. | 0.108 | 0.111 | 0.027 | | 0.133 | 0.083 | 0.000 | 0.098 | 0.175 | 0.014 |
| CE048-2602 | Mean | 0.636 | 0.527 | 0.007 | 0.006 | 0.087 | 0.045 | 0.000 | 0.106 | 0.040 | 0.015 |
| (35S-Cry1Ab) | st. dev. | 0.16 | 0.046 | 0.002 | 0.002 | 0.044 | 0.007 | 0.000 | 0.011 | 0.013 | 0.004 |
| Control 1 | Mean | 0.000 | 0.000 | 0 | 0 | 0 | 0 | 0 | 0 | 0.001 | 0 |
| (non-transformed) | st. dev. | 0.000 | 0.000 | 0 | 0 | 0 | 0 | 0 | 0 | 0.002 | 0 |
| Control 2 | Mean | 0.000 | 0.000 | 0 | 0 | 0 | 0 | 0 | 0 | 0 | 0 |
| (non-transformed) | st. dev. | 0.000 | 0.000 | 0 | 0 | 0 | 0 | 0 | 0 | 0 | 0 |
| CE0104-0202 | Mean | 0.022 | 0.023 | 0.008 | 0.017 | 0.023 | 0.016 | 0.0001 | \ | \ | \ |
| (Gos/cab-Cry1Ab) | st. dev. | 0.009 | 0.005 | 0.005 | 0.004 | 0.012 | 0.005 | 0.000 | | | |
| CE1014-0402 | Mean | 0.025 | 0.017 | 0.007 | 0.010 | 0.028 | 0.034 | 0.000 | 0.010 | 0.040 | 0.002 |
| (Gos/cab-Cry1Ab) | | 0.005 | 0.003 | 0.001 | 0.003 | 0.017 | 0.013 | 0.000 | 0.003 | 0.020 | 0.001 |

Leaf parts were cut out 2 to 3 mm around the wound, and were incubated for 18 hours in a growth chamber at 20° C. in a petri dish on a filter paper moistened with Murashige and Skoog medium (MS medium, see Plant Molecular Biology Labfax (1993) by R. D. D. Croy, jointly published by BIOS Scientific Publications Ltd (UK) and Blackwell Scientific Publications, UK, for composition). Control leaf pieces of similar size were cut from plants and were put immediately on dry ice for protein measurement (without in vitro incubation). Means represent averages of 5 plants per transformation event Expression of the Cry1Ab protein was again either absent or around the detection limit in leaves, stalk and kernels of the different TR2'-cry1Ab events tested. No significant expression was found in leaves and pollen in V4 and flowering plant stage. Constitutive expression of around 0.02-0.03% total soluble protein was seen in the roots for these plants. When leaves are mechanically damaged, expression of the Cry1Ab protein is induced and goes up to 0.05-0.1%. The 35S-cry1Ab events showed constitutive expression of the Cry1Ab protein

TABLE 4

Cry1Ab concentration in TR2'-Cry1Ab plants (wounding by insect feeding).

| Sample | | time (h) | Cry1Ab % damage by L2 ECB feeding WI602-0402 |
|---|---|---|---|
| Undamaged | on plant | 0 | 0.000 |
| | | | 0.000 |
| damaged | on plant, sample injury | 60 | 0.006 |
| | | | 0.001 |
| damaged | on plant, 2 cm above injury, dir. Stem | 60 | 0.000 |
| | | | 0.000 |
| damaged | on plant, 2 cm down injury, dir. Leaf tip | 60 | 0.000 |
| | | | 0.000 |

TABLE 4-continued

Cry1Ab concentration in TR2'-Cry1Ab plants (wounding by insect feeding).

| Sample | | time (h) | Cry1Ab % damage by L2 ECB feeding WI602-0402 |
|---|---|---|---|
| damaged | on plant, 10 cm above injury, dir. Stem | 60 | 0.000 |
| | | | 0.000 |
| damaged | on plant, 10 cm down injury, dir. Leaf tip | 60 | 0.000 |
| | | | 0.000 |
| damaged | on plant, leaf above damaged leaf | 60 | 0.000 |
| | | | 0.000 |

In a further assay, five plants in VT stage of events WI604-1602 and WI606-1206 were damaged with a scalpel in the greenhouse. Of each plant, forty hours later, samples were taken of the damaged leaf area (typically 2 to 3 mm around the wound site), from the same leaf 2 cm and 10 cm up and down of the damaged area, and from a leaf higher and lower than the wounded leaf. Leaf samples were also collected at the start of the experiment. Cry1Ab ELISA was run on the samples; mean (bold) and standard deviation were calculated. Results are shown in Table 5 below.

TABLE 5

Cry1Ab concentration in TR2'-Cry1Ab plant lines (wounding by scalpel).

| | | | Cry1Ab % damage with scalpel | |
|---|---|---|---|---|
| Sample | | time (h) | WI604-1602 | WI606-1206 |
| undamaged | on plant | 0 | 0.001 | 0.000 |
| | | | 0.001 | 0.000 |
| undamaged | on plant | 40 | 0.001 | 0.000 |
| | | | 0.001 | 0.001 |
| damaged | on plant, sample injury | 40 | 0.005 | 0.006 |
| | | | 0.001 | 0.002 |
| damaged | on plant, 2 cm above injury, dir. stem | 40 | 0.000 | 0.001 |
| | | | 0.001 | 0.001 |
| damaged | on plant, 2 cm down injury, dir. leaf tip | 40 | 0.001 | 0.001 |
| | | | 0.001 | 0.001 |
| damaged | on plant, 10 cm above injury, dir. stem | 40 | 0.001 | 0.001 |
| | | | 0.000 | 0.001 |
| damaged | on plant, 10 cm down injury, dir. leaf tip | 40 | 0.001 | 0.001 |
| | | | 0.000 | 0.000 |
| damaged | on plant, leaf above damaged leaf | 40 | 0.001 | 0.000 |
| | | | 0.001 | 0.000 |
| damaged | on plant, leaf down of damaged leaf | 40 | 0.000 | 0.000 |
| | | | 0.001 | 0.000 |

Measurements in additional field trials confirmed the low basal expression levels of the Cry1Ab protein in plants (using fresh leaf material taken from the plants, not incubated in vitro). In a field trial with 5 inbred plant lines per event comprising the pTR2'-Cry1Ab construct, between 0.001 and 0.003% of total soluble leaf protein was Cry1Ab protein (mean of 5 plants per event (standard deviation on average 0.001 to 0.004%)) in the field. An additional field trial showed that more Cry1Ab protein is found in corn plants artificially infested by ECB larvae in the field than in plants not infested with insects. The expression levels for Cry1Ab found in this trial (8 plants) were on average between 0.001 and 0.002% of total soluble protein in vegetative leaf, between 0.003 and 0.046% of total soluble protein in R1 leaf, and between 0.009 and 0.017% of total soluble protein in R5-6 leaf (using fresh leaf material taken from the plants, not incubated in vitro). As expected, insect infestation in the field provided for increased Cry1Ab protein concentration in some plants (samples were taken at random from the plants).

Example 3

Insect Resistance of Plants With Wound-Inducible Expression

A) Efficacy Against Controlled Infestation with ECB Fourth Instar Larvae.

Mid whorl corn plants were placed in a plexiglass cylinder and infested with 10 or 15 fourth instar European corn borer larvae. After 10 days, plants were dissected and percentage survival of larvae was scored per plant. The results are provided in Table 6.

TABLE 6

Efficacy against fourth instar ECB larvae

| Event | Number of plants tested | Averaged percentage survival (s.d.) |
|---|---|---|
| WI602-0402 | 6 | 0 |
| WI602-0802 | 6 | 0 |
| WI604-1602 | 6 | 0 |
| WI606-0802 | 6 | 0 |
| WI606-1206 | 6 | 0 |
| B73 control | 9 | 49.6 (18.8) |

The efficacy of the control of fourth instar ECB larvae in controlled infestation was found to be 100% for all TR2'-cry1Ab plants tested. Control plants showed on average a maximum of 50% mortality. As the fourth instar ECB larvae are believed to be between 25 and 100 times less susceptible to the modified Cry1Ab protein than first instar larvae, the level of protein produced in the TR2'-cry1Ab plants can be considered 'high dose', even though expression values as measured in such plants after wound-induction are typically still relatively low.

B) Efficacy Against ECB

Fourteen events were evaluated for ECB efficacy in the greenhouse and in field trials (Table 7).

TABLE 7

ECB Efficacy in greenhouse and field trials

| Event | ECB efficacy Greenhouse Average(sd)/max length/pl | ECB efficacy Field 1 Average(sd)/max length/pl | ECB efficacy Field 2 Average(sd)/max length/pl |
|---|---|---|---|
| WI602-0402* | 0.1(0.31)/1 | 0.24(0.41)/2 | 0.21(0.01)/2 |
| WI604-1602* | 0.2(0.42)/1 | 0.05(0.071)/1 | |
| WI606-0406* | 51.3(73.5)/195 | 8.41(1.8)/32 | 7.45(0.07)/30 |
| WI606-0802* | 3.3(2.6)/8 | 0(0)/0 | 0.05(0.07)/1 |
| WI606-1206* | 0.38(0.74)/2 | 0.17(0.29)/3 | 0.1(0.14)/1 |
| WI600-0218 | 2.0(1.87)/6 | | |
| WI600-1402 | 29.4(45.8)/142 | 6.55(2.47)/28 | |
| WI602-0202 | 168.5(26.9)/200 | 12.6(3.8)/31 | |
| WI604-0604 | 102.5(83)/251 | 3.7(2.0)/25 | |

TABLE 7-continued

ECB Efficacy in greenhouse and field trials

| Event | ECB efficacy Greenhouse Average(sd)/max length/pl | ECB efficacy Field 1 Average(sd)/max length/pl | ECB efficacy Field 2 Average(sd)/max length/pl |
|---|---|---|---|
| WI602-0802 | 0(0)/0 | 0.33(0.15)/3 | |
| WI602-0204 | 66(68.2)/160 | | |
| WI602-1002 | 102.4(63.4)/215 | | |
| WI606-0602 | 45.5(52.8)/160 | | |
| WI600-0802 | 0.9(1.44)/4 | 0.06(0.11)/2 | 0(0)/0 |

Results are presented as average length of tunnels (with standard deviation value between brackets) over maximum length of tunnels for each plant (average (sd)/max length/pl). In the greenhouse, average length of tunnels was taken of measurements on 10 plants. In the field, ECB efficacy is expressed as the average of 3 values obtained for different groups of 10 plants. Four of the five single-copy events (indicated by an asterisk) gave total ECB2 control, determined as less than 3.5 cm average tunnel length No penalty on agronomic performance was observed for the plants after second selfing (ear to row) of the different TR2' events in any of the locations tested.

Efficacy Against *Sesamia nonagrioides*

Five mid whorl corn plants comprising the TR2'-cry1Ab construct were each infested with two egg masses. Damage was scored after 14 days and the number of larvae was counted. Damage ratings (expressed in plant height and length of tunnels per plant in cm) were averaged over the five plants. Results are given in Table 8.

TABLE 8

| Event | Number of larvae per plant | Plant height in cm | Cm tunnels per plant |
|---|---|---|---|
| WI600-0802 | 0.6 (1.3) | 198 (8.4) | 0 |
| B73 Control | 197.2 (14.0) | 84 (5.5) | 70 (9.4) |

The results indicate that there is also good control of the Mediterranean stalk borer in the TR2'-cry1Ab plants tested.

Example 4

Comparative Analysis

Analysis of expression using the MPI promoter (described by Breitler et al., 2001 as being a wound-induced promoter) in corn plants with the same Cry1Ab coding sequence as used above is done to compare basal (non-induced) levels and wound-induction in the field. Corn plants expressing the insecticidal Cry1Ab protein portion under control of this MPI promoter show a basal mean expression level of at least about 0.04% Cry1Ab protein per total soluble protein in leaves in greenhouse tests. In addition, in initial greenhouse tests using 2 MPI-Cry1Ab events, some variation in expression levels upon wounding is found. However, a wound-induced increase in Cry1Ab protein (mean) expression of at least 5 times that of the basal (mean) level is not observed in these events (after mechanical wounding), when measuring the concentration both in plant material freshly taken from these plants and in detached leaf parts that are incubated in vitro. In both cases, concentration is measured in different samples at 21 hours and 42 hours after wounding. Hence, there is either no or only a weak induction of Cry1Ab protein expression (compared to the basal protein expression level) in these assays with the MPI promoter.

Also, in comparative analysis, the performance in the field of the plants of the invention, using the TR2' promoter, is compared to commercially available corn plants expressing a Cry1Ab protein portion. In these assays, corn plants obtained from events MON810 and Bt11 (see published USDA petitions of these approved corn events for a detailed description), which use a 35S promoter for high constitutive expression levels, and which are known to provide high dose insect resistance, are used.

In one field trial, the mean tunnel length (in cm per stalk, measured after stalk splitting as described in Jansens et al. (1997)) for artificial infestation with European corn borer is 0, 0, 0.04, 0, and 0.21 cm, respectively, for 5 different Cry1Ab-TR2' corn events. The mean tunnel length for MON810 corn is 0.3 and for Bt11 corn 0.13 (in non-transformed control corn lines, tunnel lengths from 12.2 to 39.92 cm are found in the same trial).

Hence, comparative analysis of the wound-induced TR2' promoter in corn shows that expression of an insecticidal protein under control of the TR2' promoter in corn provides high-level insect resistance comparable to that obtainable with commercially available events with constitutive promoters.

In another field trial, the mean tunnel length (in cm per stalk, measured after stalk splitting as described in Jansens et al. (1997)) for artificial infestation with Southwestern corn borer is 0.53, 0.68, 0.3, 0.64, and 0.6 cm, respectively, for the 5 different Cry1Ab-TR2' corn events, while the mean length for MON810 corn is 0.43 and for Bt11 corn 0.15. In non-transformed control corn lines, tunnel lengths from 32 to 39.6 cm are found in the same trial, and some have no plants standing anymore by stalk breakage due to the tunnels.

REFERENCES

Barton et al. 1987, Plant Physiol 85:1103-1109
Bradford, 1976, Anal. Biochem. 72: 248-254
Breitler et al. 2001, Mol Breeding 7: 259-274
Chen et al., 1994, Theor Appl Genet 88:187-192
Cornelissen & Vandewiele, 1989, Nucleic Acids Research 17:19-23
Clark et al., 1986, Methods Enzymol. 118:742-766.
Crickmore et al. (1998) Microbiol. Mol. Biol Rev. 62(3), 807-13.
Datta et al., 1999, Methods Mol Biol 111:335-347
De Block et al. 1989, Plant Physiol 914:694-701
De Greve et al., 1983, J Mol Applied Gen: 499-511
De maagd et al. 1999, Trends Plant Sci 4:9-13
de Pater et al., 1992, Plant J 2:837-844
Depicker et al., 1982, J Mol Appl Gen 1: 561-573
D'Halluin et al., 1992, Plant Cell 4: 1495-1505
Duan et al., 1996, Nature Biotech 14:494-498
Estruch et al. 1996, Proc Natl Acad Sci 93:5389-5394
Estruch et al. 1997, Nature Biotechn 15:137-140
Forst et al., 1997, Ann Rev Microbiol 5:47-72
Fox et al., 1992, Plant Mol Biol 20:219-233
Franck et al. 1980, Cell 21: 285-294
Gielen et al., 1984, EMBO J 3: 835-846
Green and Ryan, 1972, Science 175:776-777
Guevara-Garcia et al., 1998, Plant J 4(3):495-505
Guthrie, 1989, Plant Breed Rev 6:209-243
Harpster et al., 1988, Molecular and General Genetics 212, 182-190.
Hilder et al. 1987, Nature 300(12):160-163

Höfte et al., 1986, Eur J Biochem 161:273-280
Höfte and Whiteley, 1989, Microbiol Rev 53(2):242-55.
Irie et al., 1996, Plant Mol Biol 30:149-157
Jansens et al., 1997, Crop Science 37(5):1616-1624
Jin et al., 2000, In Vitro Cell Dev Biol—Plant 36:231-237
Langridge et al. 1989, Proc Natl Acad Sci USA 86:3219-3223
Luan et al. 1992, Plant Cell 1992, 4:971-981
Ni et al. 1995, Plant J 7(4)661-676
Odell et al. (1985) Nature 313: 810-812
Peferoen & Van Rie, 1997, Chemistry of Plant Prot 13:125-156
Peferoen 1997 in Advances in Insect Control, Taylor & Francis Ltd, London, 21-48
Poulsen, 1996, Plant Breeding 115:209-225
Reynaerts & Jansens, 1994, Acta Horticulturae 376:347-352
Shimamoto, 1994, Curr Opin Biotech 5:158-162
Thompson et al., 1987, EMBO J 6: 2519-2523
Vaeck et al., 1987, Nature 327(6125):33-37
Velten et al. 1984, EMBO J. 12:2733-2730
Wilbur and Lipmann, 1983, Proc Natl Acad Sci U.S.A. 80:726
Witowsky & Siegfried, 1997, PBI Bulletin 14-15
Zhao et al., 1996, Plant Physiol 111:1299-1306

The invention claimed is:

1. An insect-resistant corn plant, comprising, stably integrated into its genome, a chimeric gene comprising a DNA sequence encoding an insecticidal *Bacillus thuringiensis* protein under control of a promoter region comprising a TR2' promoter, wherein said plant expresses a high dose of said insecticidal protein, wherein said high dose is a concentration of said insecticidal protein in said plant which kills a developmental stage of a target insect which is between 25 to 100 times less susceptible to the insecticidal protein than the first larval stage of said insect, and wherein said target insect is the European corn borer.

2. The plant of claim 1, wherein said corn plant kills at least 97% of fourth instar European corn borer larvae in a 10 day bio-assay.

3. The plant of claim 1, wherein said TR2' promoter is the promoter of SEQ ID NO: 1.

4. A method for obtaining wound-induced, high dose, expression of an insecticidal toxin in a corn plant, said method comprising stably introducing into the plant a foreign DNA comprising a chimeric gene comprising:

a DNA sequence encoding a *Bacillus thuringiensis* insecticidal protein, and a plant-expressible promoter region comprising a TR2' promoter, wherein said high dose is a concentration of said insecticidal protein in said plant which kills a developmental stage of a target insect which is between 25 to 100 times less susceptible to the insecticidal protein than the first larval stage of said insect, and wherein said target insect is the European corn borer.

5. The method of claim 4, wherein said corn plant kills at least 97% of fourth instar European corn borer larvae in a 10 day bio-assay.

6. The method of claim 4, wherein said wound-induced expression comprises a mean basal expression level of the insecticidal protein in leaves of said plant of 0.005 percent of total soluble protein or less in greenhouse-grown plants.

7. A method for making an insect resistant corn plant expressing a high dose of an insecticidal protein, said method comprising stably introducing into the genome of said plant a foreign DNA comprising a chimeric gene comprising:
    a DNA sequence encoding a *Bacillus thuringiensis* insecticidal protein, and
    a plant-expressible promoter region comprising a TR2' promoter,
    wherein said high dose is a concentration of said insecticidal protein in said plant which kills a developmental stage of a target insect which is between 25 to 100 times less susceptible to the insecticidal protein than the first larval stage of said insect, and wherein said target insect is the European corn borer.

8. The method of claim 7, wherein said corn plant kills at least 97% of fourth instar European corn borer larvae in a 10-day bio-assay.

9. The method of claim 7, wherein said wound-induced expression comprises a mean basal expression level of the insecticidal protein in leaves of said plant of 0.005 percent of total soluble protein or less in greenhouse-grown plants.

10. A method for obtaining increased expression of an insecticidal protein in a corn plant upon wounding, wherein the mean expression level in the leaves of said plant in the greenhouse, in the absence of wounding is 0.005% of total soluble protein or less, and upon wounding said mean expression level increases at least 5-fold, said method comprising stably introducing into the genome of said plant a foreign DNA comprising a chimeric gene comprising:
    a DNA sequence encoding a *Bacillus thuringiensis* insecticidal protein, and
    a plant-expressible promoter region comprising a TR2' promoter.

11. The method of claim 10, wherein said corn plant kills at least 97% of fourth instar European corn borer larvae in a whole plant bio-assay of 10 days.

12. The method of claim 10, wherein said basal expression of 0.005% or less is measured in V4 stage leaves.

13. The method of claim 10, wherein said insecticidal protein is a Bt protein.

14. The method of claim 13, wherein said Bt protein is selected from the group consisting of Cry1Ab, Cry1F, Cry2Ae, Cry9C and Cry2Ab and insecticidal fragments thereof.

15. The plant of claim 1 wherein said Bt protein is selected from the group consisting of Cry1Ab, Cry1F, Cry2Ae, and Cry2A and insecticidal fragments thereof.

16. The plant of claim 1, wherein said wound-induced expression comprises a mean basal expression level of the insecticidal protein in leaves of said plant of 0.005 percent of total soluble protein or less in greenhouse-grown plants.

17. The plant of claim 1, wherein said TR2' promoter is a promoter region comprising a fragment of SEQ ID NO:1 from a nucleotide position between nucleotide positions 1 and 336 to nucleotide position 483.

18. The plant of claim 1, wherein said TR2' promoter comprises the sequence of nucleotides 96 to 483 of SEQ ID NO:1.

19. The method of claim 4, wherein said TR2' promoter is a promoter region comprising a fragment of SEQ ID NO:1 from a nucleotide position between nucleotide positions 1 and 336 to nucleotide position 483.

20. The method of claim 4, wherein said TR2' promoter comprises the sequence of nucleotides 96 to 483 of SEQ ID NO:1.

21. The method of claim 7, wherein said TR2' promoter is a promoter region comprising a fragment of SEQ ID NO:1 from a nucleotide position between nucleotide positions 1 and 336 to nucleotide position 483.

22. The method of claim 7, wherein said TR2' promoter comprises the sequence of nucleotides 96 to 483 of SEQ ID NO:1.

23. The method of claim 10, wherein said TR2' promoter is a promoter region comprising a fragment of SEQ ID NO:1 from a nucleotide position between nucleotide positions 1 and 336 to nucleotide position 483.

24. The method of claim 10, wherein said TR2' promoter comprises the sequence of nucleotides 96 to 483 of SEQ ID NO:1.

25. A corn plant comprising a DNA sequence encoding a *Bacillus thuringiensis* protein insecticidal to a target insect species feeding on said plant, said DNA sequence being operably-linked to a plant-expressible promoter region, wherein the concentration of said insecticidal protein in said plant is such that it kills a developmental stage of said target insect species which is between 25 to 100 times less susceptible to the toxin than the first larval stage of said insect, and wherein said plant has a mean expression level in its leaves of said insecticidal protein, in the absence of wounding or insect feeding, of 0.005% of total soluble protein or less, and wherein said plant-expressible promoter region comprises a TR2' promoter and wherein said target insect is the European corn borer.

26. The plant of claim 25, wherein said *Bacillus thuringiensis* protein is selected from the group consisting of Cry1Ab, Cry1F, Cry2Ae, Cry9C and Cry2Ab and insecticidal fragments thereof.

27. The method of claim 10, wherein said *Bacillus thuringiensis* protein is selected from the group consisting of Cry1Ab, Cry1F, Cry2Ae, Cry9C and Cry2Ab and insecticidal fragments thereof.

* * * * *